US011406257B2

(12) United States Patent
Lane et al.

(10) Patent No.: US 11,406,257 B2
(45) Date of Patent: Aug. 9, 2022

(54) VISION SCREENING DEVICE AND METHODS

(71) Applicant: Welch Allyn, Inc., Skaneateles Falls, NY (US)

(72) Inventors: John A. Lane, Weedsport, NY (US); Chris R. Roberts, Skaneateles, NY (US); David L. Kellner, Baldwinsville, NY (US); Eric J. Laurin, Beaverton, OR (US); Zachary K. Boronka, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 490 days.

(21) Appl. No.: 16/522,028

(22) Filed: Jul. 25, 2019

(65) Prior Publication Data

US 2020/0029802 A1     Jan. 30, 2020

Related U.S. Application Data

(60) Provisional application No. 62/711,461, filed on Jul. 27, 2018.

(51) Int. Cl.
*A61B 3/00* (2006.01)
*A61B 3/113* (2006.01)
*G16H 50/20* (2018.01)

(52) U.S. Cl.
CPC ............ *A61B 3/0025* (2013.01); *A61B 3/113* (2013.01); *G16H 50/20* (2018.01)

(58) Field of Classification Search
CPC ......... A61B 3/0025; A61B 3/113; A61B 3/02; A61B 3/11; A61B 3/18; A61B 3/103; G16H 50/20

(Continued)

(56) References Cited

U.S. PATENT DOCUMENTS 6,523,954 B1   2/2003  Kennedy et al.
7,206,435 B2   4/2007  Fujimura et al.
(Continued)

FOREIGN PATENT DOCUMENTS

JP   2014083095    5/2012
KR   20060022935   3/2006
(Continued)

OTHER PUBLICATIONS

Zou et al., "Ambient Illumination Variation Removal by Active Near-IR Imaging," Centre for Vision, Speech, and Signal Processing, Univ. of Surrey, United Kingdom, D. Zhang and A.K. Jain (Eds.): ICB 2006, LNCS 3832, pp. 19-25, 2005. Springer-Verlag Berlin Heidelberg 2005.

(Continued)

*Primary Examiner* — Mohammed A Hasan
(74) *Attorney, Agent, or Firm* — Lee & Hayes, P.C.

(57) ABSTRACT

A vision screening system for testing the vision of a patient is described herein. The vision screening system may include a vision screening device configured to perform a number of vision screening tests. For example, the system may be configured to determine or generate a graphical representation for display to the patient, via the vision screening device, to evaluate the health of the patient's vision and/or detect abnormal vision behavior. The system may be configured to evaluate image/video data recorded by the vision screening device to determine measurements associated with the patient during the vision screening. The system may be configured to analyze the measurements to generate a diagnosis recommendation associated with the vision of the patient. The system may also be configured to display the recommendation and/or the measurements, along with additional screening data, to a tester conducting the vision test.

16 Claims, 9 Drawing Sheets

(58) Field of Classification Search
USPC .......................................................... 351/209
See application file for complete search history.

(56) References Cited

U.S. PATENT DOCUMENTS

| | | | | |
|---|---|---|---|---|
| 9,332,901 | B2 | 5/2016 | Eraluoto | |
| 9,433,346 | B2* | 9/2016 | Huang | |
| 10,558,783 | B2* | 2/2020 | Ahmed | G16H 30/40 |
| 2004/0141152 | A1* | 7/2004 | Marino | A61B 3/032 |
| | | | | 351/222 |
| 2009/0079937 | A1* | 3/2009 | Chen | A61B 3/145 |
| | | | | 351/210 |
| 2009/0290772 | A1* | 11/2009 | Avinash | G16H 30/20 |
| | | | | 382/130 |
| 2012/0239434 | A1* | 9/2012 | Breslow | G16H 50/20 |
| | | | | 705/3 |
| 2014/0253876 | A1 | 9/2014 | Klin | |
| 2015/0362991 | A1* | 12/2015 | Koga | G06F 3/0482 |
| | | | | 715/810 |
| 2017/0325675 | A1 | 11/2017 | Liu | |
| 2018/0140178 | A1 | 5/2018 | Anderson et al. | |
| 2018/0149874 | A1 | 5/2018 | Aleem et al. | |
| 2018/0014723 | A1 | 6/2018 | Hane et al. | |

FOREIGN PATENT DOCUMENTS

| | | |
|---|---|---|
| WO | WO2017094343 A1 | 6/2017 |
| WO | WO2018055618 | 3/2018 |

OTHER PUBLICATIONS

The Extended European Search Report dated Jan. 13, 2020 for European Patent Application No. 19188470.9, 7 pages.

European Office Action dated Feb. 23, 2022 for European Patent Application No. 19188470.9, a foreign counterpart to U.S. Appl. No. 16/522,028, 123 pages.

* cited by examiner

VISION SCREENING DEVICE AND METHODS

CROSS REFERENCE TO RELATED APPLICATIONS

This application is a nonprovisional of and claims priority to U.S. Provisional Application No. 62/711,461, filed Jul. 27, 2018, entitled "Vision Screening Device and Methods," the entire disclosure of which is incorporated herein by reference.

TECHNICAL FIELD

This application is directed to medical equipment, and in particular, to a vision screening device configured to determine refractive error, convergence, visual acuity, and/or other vision screening parameters.

BACKGROUND

Visual screening in children and adults typically includes one or more tests to determine various deficiencies associated with the patient's eyes. Such tests may include, for example, refractive error tests, convergence tests, accommodation tests, visual acuity tests, and the like. While one or more of the above tests may be related, each test has a respective purpose. For instance, visual acuity testing typically relies on a person reading characters printed on a Snellen chart at a given distance. That person's visual acuity is based on which size of characters on the chart the person can discern. The test usually begins with the person reading the top-most, largest character while covering one eye. Then the person proceeds to read each character in each line until they are no longer able to discern the characters. The process repeats for the opposite eye. A person with "normal vision" of 20/20 will read about 30 characters on the Snellen chart for each test.

While various vision screening devices exist, such devices are typically cumbersome and complicated to use. As a result, vision screening determinations made using such devices may lack accuracy and consistency. Additionally, while such devices may be designed to perform one of the above tests above, such devices are generally not configured to perform multiple vision screening tests. Thus, such devices lack utility.

The various example embodiments of the present disclosure are directed toward overcoming one or more of the deficiencies associated with known vision screening devices.

BRIEF DESCRIPTION OF THE DRAWINGS

Features of the present disclosure, its nature and various advantages, may be more apparent upon consideration of the following detailed description, taken in conjunction with the accompanying drawings.

In the figures, the left-most digit(s) of a reference number identifies the figure in which the reference number first appears. The use of the same reference numbers in different figures indicates similar or identical items or features. The drawings are not to scale.

DETAILED DESCRIPTION

Figure 1:
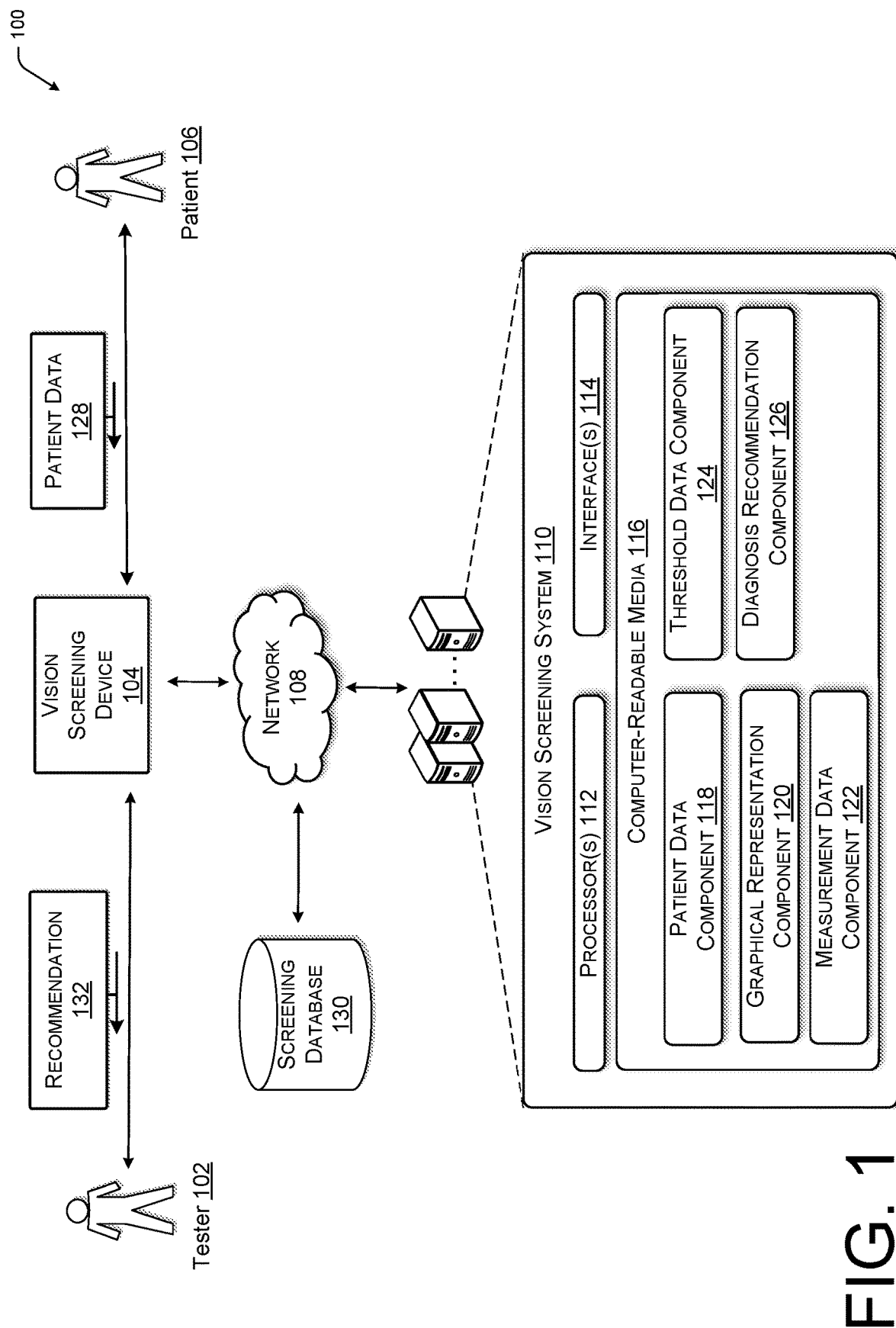
FIG. 1 illustrates an example environment for vision screening according to some implementations.

Techniques described herein are directed to, in part, a vision screening system. Such an example vision screening system may be configured to perform one or more vision tests on a patient and to output the results of the vision test(s) to a user of the device, such as a physician or a physician's assistant. For example, the vision screening system may generate one or more graphical representations, such as a paragraph of text or a dynamic image, for display to the patient. While the patient is viewing the graphical representation, the system may collect one or more measurements associated with the eyes of the patient, such as a diameter of the lens of the eye, a location of the pupils, or a gaze of the patient. As such, the results may include one or more measurements detected throughout the vision screening test. In addition, the system may generate a recommendation and/or diagnosis associated with the patient for display to the tester.

As is known, conventional vision screening techniques are often conducted by an individual, such as a physician or other person qualified to conduct a vision screening test (e.g., a nurse, technician, etc.). For example, the physician may display a visual, such as a light or Snellen chart, to a patient and may observe the response of the eyes to the visual (e.g., observe how the pupils of the patient expand or contract, determine the gaze direction of the patient, etc.) and/or ask the patient to interact with the visual (e.g., read the letters of the Snellen chart). In these examples, the physician may rely on the patient to provide accurate feedback and/or may rely on their own ability to observe the reactions of the different parts of the eye in response to the visual. For example, the physician may simply observe the expansion and contraction of the pupils in response to a light or how well the patient's eyes follow the light when it moves.

Because such tests rely on patient feedback and/or the observations of the individual conducting the vision screening test, the results are often unreliable and inaccurate. For example, if the physician is manually monitoring, or observing, how the patient's pupils track a visual, the results of the test may not be fully accurate. Additionally, there is no record of the patient's response, and therefore the patient's vision quality may not be tracked accurately over time.

Further, as described herein, conventional systems often are not configured to perform multiple vision screening tests or to record multiple types of measurements, produce different results, etc. For example, a conventional system may be configured only to provide refraction measurements for a patient and additional systems or devices may be required to perform additional tests and to gather additional information about the patient's eye health. The techniques for vision screening described herein, however, help to provide more accurate, reliable, and efficient vision screening testing for both the patients and individuals conducting the screening alike.

The techniques and systems described herein, allow for more efficient vision screenings to be conducted with more accurate results achieved. For example, the system discussed herein is configured to perform multiple, dynamic vision screening tests. In some embodiments, the system may be configured to generate different types of graphical representations or visual stimuli to record multiple types of measurements associated with the patient's vision. In this way, the system may provide different types of information regarding the vision and eye health of the patient without the need for multiple devices.

Further, the system described herein is configured to record different types of vision screening tests to determine more accurate measurements associated with the eye behavior of the patient. For example, the system described herein may be configured to track the movement of the pupils of a patient to determine pupil behavior and directions of the patient's gaze in response to the graphics shown during the vision screening test. As such, the system is able to provide accurate, recorded measurements of the eye's behavior throughout the vision screening test and provide the measurements to the individual conducting the vision screening. By recording the measurements, and generating corresponding video data, the vision health of the patient may be tracked over time to provide more accurate and timely diagnosis recommendations.

Still further, the system described herein may be configured to provide diagnosis recommendations to the individual conducting the vision screening. For example, by utilizing standard testing data and/or machine learning techniques, the system may evaluate the measurements determined by the system to provide a recommendation to the individual regarding the vision of the patient (e.g., whether the patient passed the test, requires additional screening, etc.). As such, the system described herein may provide automated diagnosis recommendations with increased efficiency and precision.

In examples described below, the system may determine, or access, patient data associated with a patient participating in a vision screening test. For example, the patient data may include data provided by the patient or accessed from a patient profile. The patient data may include demographic information (e.g., age, ethnicity, gender, etc.), physical characteristics of the patient (e.g., height), and the like. In examples, the patient data may include information determined by the vision screening system. For example, the vision screening system may include a device that may record audio/video data associated with the patient at the onset of the screening that may be used to determine data associated with the patient such as height, location of the patient's eyes, a distance of the patient from the screening device, and the like. Further, a user, such as the tester or person operating the vision screening device, may provide, or input, the information to the system during the vision screening. Still further, the patient data may be imported to the system from a database storing the patient data locally or remotely.

In examples, the system may identify a testing category associated with the patient, or patient, based on the patient data. For example, depending on the age, height, or gender of the patient, the system may determine a category associated with the patient. Based on the testing category, the system may generate the appropriate graphical representation to display to the patient during the vision screening. For example, if the patient data indicates that the patient is a toddler, the system may generate a graphical representation to conduct a vision screening of a toddler of the patient's age, height, gender, etc. The graphical representation may be configured to induce a strain on the vision, or eyes, of the patient during the vision screening test. For example, the graphical representation may include a light stimulus, an augmented or virtual reality rendering, a depiction, text, and the like.

The system may determine one or more measurements associated with the vision of the patient, such as measurements associated with the eyes of the patient. For example, the system may determine a direction of the patient's gaze, a location of the pupils of the patient, an accommodation or adjustability associated with the lenses, motion of the eyes, and the like, of the patient throughout the vision screening. As an example, the patient may be shown a graphical representation including a moving graphic. As the graphic moves, the direction of the patient's gaze may be tracked and utilized to determine a location of the pupils of the patient at different points in time of viewing the graphic may be determined.

In examples, the system may compare the measurements with standard, or predetermined, measurements known to be associated with normal vision health or behavior. For example, known thresholds of normal eye behavior associated with the graphic representations presented and/or the testing category associated with the patient may be compared to the determined measurements to determine whether the patient's eyes are functioning according to the known standards. Depending on whether or not the measurements satisfy the known threshold(s) and/or are within the threshold value(s), the system may generate a diagnosis recommendation associated with the patient. For example, if the measurements satisfy the known threshold(s), the system may generate a recommendation indicating that the patient has passed the vision screening. If the measurements do not satisfy the known threshold(s), the system may generate a recommendation including an indication that the patient has failed the screening, an indication of a diagnosis, or a recommendation for additional screening. In examples, the system may also utilize one or more machine learning techniques to generate the diagnosis recommendation. The recommendation, along with the measurements, may be presented to the tester via an interface of the device.

In other examples, the system may further generate audio and/or video data associated with the vision screening. For example, the system may record the patient during the vision screening and may utilize the video data to determine the one or more measurements and/or generate additional video data. As an example, the system may utilize the video data of the patient during the screening to generate one or more data points associated with the location of the patient's pupils at points in time viewing the graphical representation. The system may then generate additional video data including the graphical representation, as well as one or more visual indicators indicating a location of the pupils throughout the vision screening test. In this way, the tester may view the video data and/or the additional video data at any time after the vision screening is complete. As such, users, such as testers, physicians, and the like, may utilize the video data to monitor the vision health of patients and make proactive diagnosis recommendations.

Additional details pertaining to the above-mentioned techniques are described below with reference to FIGS. 1-9. It is to be appreciated that while these figures describe example environments and devices that may utilize the claimed techniques, the techniques may apply equally to other environments, devices, and the like.

FIG. 1 illustrates an example environment for vision screening according to some implementations. As illustrated in FIG. 1, the environment 100 includes a tester 102 administering a vision screening, via a vision screening device 104, on a patient 106 to determine vision health of the patient 106. As described herein, the vision screening device 104 may perform one or more vision screening tests to determine one or more measurements associated with the patient 106 and provide the measurement(s), via a network 108, to a vision screening system 110 for analysis. In response, the vision screening system 110 may analyze the measurement(s) to diagnosis the vision health of the patient 106. It should be understood that, while FIG. 1 depicts one system, vision screening system 110, the environment 100 may include any number of systems configured to operate independently and/or in combination and configured to communicate with each other via the network 108. The components of the vision screening system 110 may be described in detail below.

In examples, the vision screening system 110 may include one or more processors 112, one or more network interfaces 114, and computer-readable media 116. The computer-readable media 116 may store one or more functional components that are executable by processor(s) 112 such as a patient data component 118, a graphical representation component 120, a measurement data component 122, a threshold data component 124, and/or a diagnosis recommendation component 126. At least some of the components, modules, or instructions of the computer-readable media 116 may be described below.

In examples, the vision screening device 104 may include a stationary or portable device configured to perform one or more vision screening tests on the patient 106. For example, the vision screening device 104 may be configured to perform a visual acuity test, a refractive error test, an accommodation test, dynamic eye tracking tests, and/or any other vision screening tests configured to evaluate and/or diagnose the vision health of the patient 106. Due to its stationary or portable nature, the vision screening device 104 may perform the vision screening tests at any location, from conventional screening environments, such as schools and medical clinics, to remote and/or mobile locations.

As described herein, the vision screening device 104 and/or vision screening system 110 may be configured to perform accommodation and refractive error testing on the patient 104. For example, refractive error and accommodation testing may include displaying a visual stimulus, such as a light or graphical representation, configured to induce a strain to the patient's 104 eyes. In response, the vision screening device 104 may detect the pupils and/or lenses of the eyes of the patient 104, acquire images and/or video data of the pupils/lenses, and the like, and may transmit the vision screening data, via the network 108, to the vision screening system 110 for analysis. Alternatively, or in addition, the vision screening device 104 may perform the analysis locally.

In examples, the vision screening device 104 may be configured to perform visual acuity testing and/or dynamic eye tracking tests. For example, the vision screening device 104 and/or the vision screening system 110 may be configured to perform visual acuity testing, which includes determining an optotype, determining a distance of the patient 106 from the vision screening device 104, and/or displaying a dynamic optotype to the patient 104. The dynamic eye tracking test may include generating a graphical representation, such as a graphic scene or text, for display to the patient 106 and monitoring the movement of the eye, acquire images and/or video data of the eyes, and the like, and may transmit the vision screening data, via the network 108, to the vision screening system 110 for analysis. Alternatively, or in addition, in some examples, the vision screening device 104 may analyze the vision screening data locally.

In examples, the patient data component 118 may be configured to store and/or access data associated with the patient 104. For example, the patient 106 may provide data, such as patient data 128, upon initiating a vision screening test. For instance, when the vision screening device 104 and/or vision screening system 110 initiates a vision screening test, the patient 106 may provide, or the tester 102 may request, the patient data 128 regarding the patient's demographic information, physical characteristics, preferences, and the like. For example, the patient 106 may provide demographic information such as name, age, ethnicity, and the like. The patient 106 may also provide physical characteristic information such as height of the patient 106. In such examples, the tester 102 may request the data while the screening is in progress, or before the screening has begun. In some examples, the tester 102 may be provided with predetermined categories associated with the patient 106, such as predetermined age ranges (e.g., six to twelve months, one to five years old, etc.), and may request the patient data 128 in order to select the appropriate category associated with the patient 106. In other examples, the tester 102 may provide a free form input associated with the patient data 128. In still further examples, an input element may be provided to the patient 106 directly.

Alternatively, or in addition, the vision screening device 104 and/or vision screening system 110 may determine and/or detect the patient data 128 during the vision screening test. For example, the vision screening device 104 may be configured to generate image and/or video data associated with the patient 106 at the onset of the vision screening test. For example, the vision screening device 104 may include one or more digital cameras, motion sensors, proximity sensors, or other image capture devices configured to collect images and/or video data of the patient 106, and one or more processors of the vision screening device 104 may analyze the data to determine the patient data 128, such as the height of the patient 106 or the distance of the patient 106 from the screening device. For example, the vision screening device 104 may be equipped with a range finder, such as an ultra-sonic range finder, an infrared range finder, and/or any other proximity sensor that may be able to determine the distance of the patient 106 from the screening device.

Alternatively, or in addition, the vision screening device 104 may be configured to transmit the images/video data to the vision screening system 110, via the network 108, for analysis to determine the patient data 128. For example, the vision screening device 104 may transmit the image/video data to the vision screening system 110 and the patient data component 118 may be configured to analyze the data to determine the patient data 128. Still further, the patient data component 118 may be configured to receive, access, and/or store patient data 128 associated with the patient 106 and/or additional patients. For example, the patient data component 118 may store previous patient information associated with the patient 104 and/or other patients who have utilized the vision screening system 110. For instance, the patient data component 118 may store previous patient preferences, screening history, and the like. The patient data component 118 may receive the patient data 128 and/or may access such information via the network 108. For example, the patient data component 118 may access an external database, such as screening database 130, storing data associated with the patient 106 and/or other patients. For example, the screening database 130 may be configured to store patient data 128 stored in association with a patient ID. When the tester 102 and/or patient 106 enters the patient ID, the patient data component 118 may access or receive the patient data 128 stored in association with the patient ID and the patient 106.

In addition, the computer-readable media 116 may store a graphical representation component 118. The graphical representation component 118 may be configured to generate or determine a graphical representation for display to the patient 106, via the vision screening device 104, during the vision screening process. For example, the graphical representation component 118 may be configured to receive and/or access patient data 128 from the patient data component 118 to determine a graphical representation to generate and/or display to the patient 106. As an example, the graphical representation component 118 may utilize the patient data 128 to determine a testing category that the patient 106 belongs to (e.g., a testing category based on age, height, etc.). Based on the patient data 128, the testing category, and/or the vision screening to be performed, the graphical representation component 118 may determine an existing graphical representation or generate a graphical representation for display to the patient 106.

For example, the patient data 128 may indicate that the patient 106 is a child between the ages of six to twelve months. Based on this information, the graphical representation component 118 may access one or more locally or remotely stored graphical representations associated with the testing category of six to twelve months. Alternatively, or in addition, the graphical representation component 118 may be configured to generate a graphical representation configured to strain the vision of the patient 106. Still further, the graphical representation component 118 may be configured to determine the graphical representation for display based on the vision screening test to be performed. In some examples, the graphical representation component 118 may determine the graphical representation for display based on more than one element of the patient data 128 and/or more than one testing category. For example, the graphical representation component 118 may be configured to determine the graphical representation for display based on both age and gender data.

The computer-readable media 116 may additionally store a measurement data component 120. The measurement data component 120 may be configured to receive, access, and/or analyze testing data collected and/or detected by the vision screening device 104 during the vision screening. For example, the measurement data component 120 may be configured to receive, via the network 108, video data generated by the vision screening device 104 of the patient 106 during the vision screening and while the graphical representation is being displayed. The measurement data component 120 may analyze the video data to determine one or more measurements associated with the patient 106, such as the gaze of the patient throughout the screening, a location of the patient's pupils at points in time of viewing the graphical representation, a diameter of the pupils, an accommodation of the lens, motion information associated with the eyes of the patient 106, and the like. Alternatively, or in addition, the measurement data component 120 may be configured to receive and/or access measurement data that has been determined by the vision screening device 104 locally.

Further, the computer-readable media 116 may be configured to store a threshold data component 124. The threshold data component 124 may be configured to receive, access, and/or analyze threshold data associated with standard testing results. For example, the threshold data component 124 may be configured to access, or receive data from, a third-party database storing testing data and/or measurements, or a range of values indicating a threshold within which testing values should lie, associated with patients having normal vision health with similar testing conditions. For example, for each testing category, standard testing data may be accessed or received by the threshold data component 124 and may be utilized for comparison against the measurement data stored by the measurement data component 122. For instance, the threshold data associated with the toddler testing category may include standard pupil measurements, and/or a threshold range of values which the testing values should not exceed or fall below (e.g., a standard value range) for toddlers when displayed each graphical representation. For example, when testing for accommodation in the patient 106, the threshold data component 124 may be configured to store information associated with the amplitude of accommodation and age (e.g., Donder's Table).

Alternatively, or in addition, the threshold data component 124 may be configured to utilize one or more machine learning techniques to determine threshold data associated with each testing category and/or graphical representation. For example, the threshold data component 124 may access and/or receive historical vision screening data from the screening database 130 and may utilize this data to train one or more machine learning models to determine standard testing measurements for each testing category. For example, machine learning component(s) (not shown) of the threshold data component 124 may execute one or more algorithms (e.g., decision trees, artificial neural networks, association rule learning, or any other machine learning algorithm) to train the system to determine the one or more threshold values based on historical vision screening data. In examples, the machine learning component(s) may execute any type of supervised learning algorithms (e.g., nearest neighbor, Naïve Bayes, Neural Networks, unsupervised learning algorithms, semi-supervised learning algorithms, reinforcement learning algorithms, and so forth).

The computer-readable media 116 may additionally store a diagnosis recommendation component 126. The diagnosis recommendation component 126 may be configured to receive, access, and/or analyze measurement data from the measurement data component 122 and/or threshold data from the threshold data component 124 for comparison. For example, the diagnosis recommendation component 126 may utilize the threshold data, learned or otherwise determined, for comparison against the measurement data to determine if the patient 106 is exhibiting normal vision behavior. For example, if the pupil diameter measurement(s) detected by the vision screening device 104 in response to the graphical representation are within a learned or known (e.g., predetermined) threshold of the standard values (e.g., if the measurements fall within a standard range) known for patients of the same testing category, the diagnosis recommendation component 126 may generate a recommendation indicating that the patient 106 has passed the vision screening. Alternatively, if the pupil diameter measurement(s) fall outside of the standard value range, the diagnosis recommendation component 126 may generate a recommendation indicating that the patient 106 has failed the vision screening test and/or indicating that the patient 106 should receive additional screening.

As used herein, network 108 is typically any type of wireless network or other communication network known in the art. Examples of network 108 include the Internet, an intranet, a wide area network (WAN), a local area network (LAN), and a virtual private network (VPN), cellular network connections and connections made using protocols such as 802.11a, b, g, n and/or ac. U.S. Pat. No. 9,237,846, filed Feb. 17, 2012, describes systems and methods for photo refraction ocular screening and that disclosure is hereby incorporated by reference in its entirety.

As described herein, a processor, such as processor(s) 112, can be a single processing unit or a number of processing units, and can include single or multiple computing units or multiple processing cores. The processor(s) 112 can be implemented as one or more microprocessors, microcomputers, microcontrollers, digital signal processors, central processing units, state machines, logic circuitries, and/or any devices that manipulate signals based on operational instructions. For example, the processor(s) 112 can be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The computer-readable media 116 may can include volatile and nonvolatile memory and/or removable and non-removable media implemented in any type of technology for storage of information, such as computer-readable instructions, data structures, program modules, or other data. Such computer-readable media 116 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the electronic negotiation system 110, the computer-readable media 116 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 116 can be used to store any number of functional components that are executable by the processor(s) 112. In many implementations, these functional components comprise instructions or programs that are executable by the processor(s) 112 and that, when executed, specifically configure the one or more processor(s) 112 to perform the actions attributed above to the service provider and/or payment service.

The network interface(s) 114 may enable wired and/or wireless communications between the components and/or devices shown in environment 100 and/or with one or more other remote systems, as well as other networked devices. For instance, at least some of the network interface(s) 114 may include a personal area network component to enable communications over one or more short-range wireless communication channels. Furthermore, at least some of the network interface(s) 114 may include a wide area network component to enable communication over a wide area network.

Figure 2:
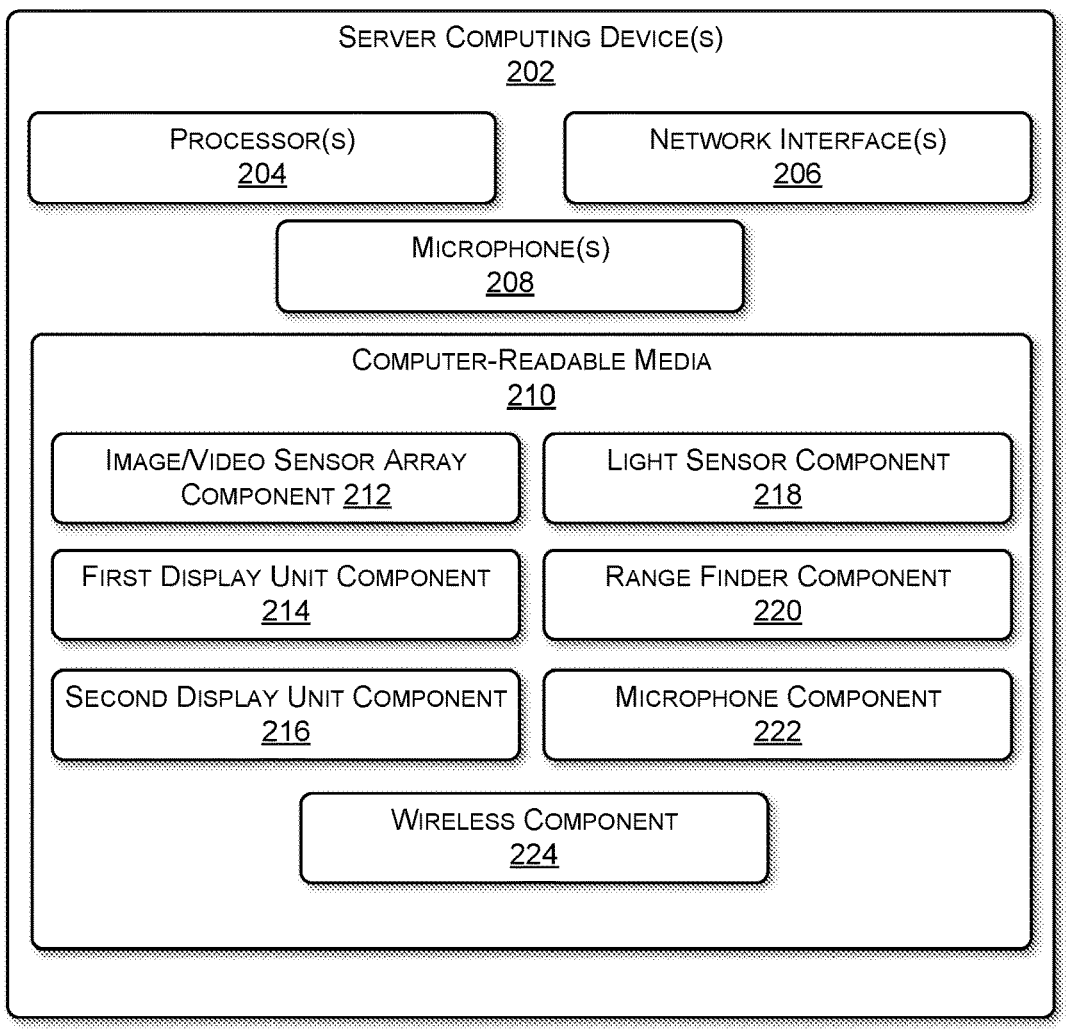
FIG. 2 illustrates an example server computing device of an example vision screening device that may be used for vision screening according to some implementations.

FIG. 2 illustrates an example server computing device 202 of a vision screening device 200 for performing techniques as described herein. As described herein, the server computing device(s) 202 ("server(s)" hereinafter) can include one or more servers or other types of computing devices that can be embodied in any number of ways. For example, in the example of a server, the modules, other functional components, and data can be implemented on a single server, a cluster of servers, a server farm or data center, a cloud-hosted computing service, a cloud-hosted storage service, and so forth, although other computer architectures can additionally or alternatively be used.

Further, while the figures illustrate the components and data of the server(s) 202 as being present in a single location, these components and data can alternatively be distributed across different computing devices and different locations in any manner. In some examples, such components and data can be distributed across user computing devices, as described herein. The functions can be implemented by one or more server computing devices, with the various functionality described above distributed in various ways across the different computing devices. Multiple server(s) 202 can be located together or separately, and organized, for example, as virtual servers, server banks and/or server farms.

In some examples, the server(s) 202 may perform the same or similar functions as the vision screening system(s) described in FIGS. 1-9. The server(s) 202 may comprise processor(s) 204 that are operatively connected to network interface(s) 206, microphone(s) 208, and a computer-readable media 210. Each processor 204 can be a single processing unit or a number of processing units and can include single or multiple computing units or multiple processing cores. The processor(s) 204 can be implemented as one or more microprocessors, microcomputers, microcontrollers, digital signal processors, central processing units, state machines, logic circuitries, and/or any devices that manipulate signals based on operational instructions. For example, the processor(s) 204 can be one or more hardware processors and/or logic circuits of any suitable type specifically programmed or configured to execute the algorithms and processes described herein. The processor(s) 204 can be configured to fetch and execute computer-readable instructions stored in the computer-readable media 210, which can program the processor(s) 204 to perform the functions described herein.

The computer-readable media 210 can include volatile and nonvolatile memory and/or removable and non-removable media implemented in any type of technology for storage of information, such as computer-readable instructions, data structures, program modules, or other data. Such computer-readable media 210 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the server(s) 202, the computer-readable media 210 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 210 can be used to store any number of functional components that are executable by the processor(s) 204. In many implementations, these functional components comprise instructions or programs that are executable by the processor(s) 204 and that, when executed, specifically configure the one or more processors 204 to perform the actions attributed above to the automated negotiation system. Functional components stored in the computer-readable media 210 can include an image/video sensor array component 212, a first display unit component 214, a second display unit component 216, a light sensor component 218, a range finder data component 220, a microphone data component 222 and/or a wireless component 224.

In some examples, the second display unit component 216 may be oriented to face the patient and the first display unit component 214 may be oriented to face the individual conducting the vision screening test, such as a physician. In other examples, the computer-readable media 210 may include an additional component (not pictured), such as a mechanical motor component, that may adjust the position of one or more components.

In examples, the computer-readable media 210 may include an image/video sensor array component 212. The image/video sensor array component 212 may be configured to receive and/or access light, image, and/or video data associated with a patient being evaluated during the vision screening. In particular, the image/video sensor array component 212 may be configured to capture, or generate, image and/or video data during the vision screening. For example, as described herein, the image data and/or video data may be generated by the image/video sensor array component 212 during the vision screening to determine initial patient data, one or more measurements associated with the body and eyes of the patient, and the like. The image/video data may be transmitted, via the network interface(s) 206, to the vision screening system for processing and analysis.

In some examples, the image/video sensor array component 212 includes, for example, a complementary metal-oxide semiconductor (CMOS) sensor array, also known as an active pixel sensor (APS), or a charge coupled device (CCD) sensor. In some examples, a lens is supported by the vision screening device 200 and positioned in front of the image sensor array component 212. In still further examples, the image/video sensor array component 212 has a plurality of rows of pixels and a plurality of columns of pixels. For example, the image/video sensor array component 212 may include approximately 1280 by 1024 pixels, approximately 640 by 480 pixels, approximately 1500 by 1152 pixels, approximately 2048 by 1536 pixels, and/or approximately 2560 by 1920 pixels. The image/video sensor array component 212 may be capable of capturing approximately 25 frames per second (fps), approximately 30 fps, approximately 35 fps, approximately 40 fps, approximately 50 fps, approximately 75 fps, approximately 100 fps, approximately 150 fps, approximately 200 fps, approximately 225 fps, and/or approximately 250 fps. Note that the above pixel values are exemplary and other values may be greater or less than the examples described herein.

In examples, the image/video sensor array component 212 may include photodiodes having a light-receiving surface and have substantially uniform length and width. During exposure, the photodiodes convert the incident light to a charge. The image/video sensor array component 212 may be operated as a global shutter. For example, substantially all of the photodiodes may be exposed simultaneously and for substantially identical lengths of time. Alternatively, the image/video sensor array component 212 may be used with a rolling shutter mechanism, in which exposures move as a wave from one side of an image to the other. Other mechanisms are possible to operate the image/video sensor array component 212 in yet other examples. The image/video sensor array component 212 may also be configured to capture digital images. The digital images can be captured in various formats, such as JPEG, BITMAP, TIFF, etc.

In examples, the computer-readable media 210 may include a first display unit component 214. The first display unit component 214 may include a graphical user interface configured to display information to the tester and/or receive input from the tester during the vision screening. For example, the first display unit component 214 may be configured to receive input from the tester regarding the patient, such as the initial patient information described herein. Further, the first display unit component 214 may be configured to display information regarding the visions screening device (e.g., the positioning of various components of the device), the distance of the patient from the device, the quality of the environment and/or the focus of the device, the progress of the screening, options for transmitting data from the device to the vision screening system and/or an external database, one or more measurements and/or the diagnosis recommendation generated during the vision screening, among others. The first display unit component 214 may comprise, for example, a liquid crystal display (LCD) or active matrix organic light emitting display (AMOLED). The first display unit component 214 may also be touch-sensitive to receive input from the tester.

In examples, the computer-readable media 210 may include a second display unit component 216. The second display unit component 216 may include one or more components configured to display one or more graphical representations to the patient during the vision screening test. For example, based on the patient data, the second display unit component 216 may be configured to generate a graphical representation for display to the patient configured to induce an eye strain. The second display unit component 216 may comprise, for example, a liquid crystal display (LCD) or active matrix organic light emitting display (AMOLED).

The second display unit component 216 may further include a light-emitting diode (LED) array including one or more visible LEDs and/or one or more near-infrared LEDs. In some examples, a beam splitter directs the light emitted from the LED array towards the patient. The near-infrared LEDs in the LED array may include a wavelength of approximately 850 nanometers (nm) and may be configured to capture video and/or image data associated with the eyes of the patient. In some examples, the visible LEDs in the LED array may include a wavelength of less than approximately 630 nm. This allows for a visual stimulus, or graphical representation, to be displayed to the patient without being seen in the image/video data captured by the image sensor array component 212. In some examples, the visible LEDs may be positioned between, and be substantially co-planar with, the near-infrared LEDs in the LED array.

In some examples, amber LEDs may be among the visible LEDs used in the second display unit component 216. Amber LEDs may include a wavelength of approximately 608 nm to approximately 628 nm. In examples, the amount of power directed to the LEDs in the LED array may be regulated by one or more components of the device, such as the second display unit component 216. For example, to minimize the pupil constriction and eye strain of the patient, the amber LEDs may be illuminated at low to medium power. For example, a 20 mA LED can be run at between approximately 2 mA to approximately 10 mA. Alternatively, low brightness amber LEDs can be used, for example, such as LEDs that run at about 0.5 mA. Additionally, LEDs can be pulse modulated. Visible light LEDs in colors other than amber, when present in the second display unit component 216, can also be operated at low to medium power.

In examples, the computer-readable media 210 may include a light sensor component 218. As described herein, the vision screening device 200 may record details of each vision screening environment. For example, the light sensor component 210 may be configured to record a light intensity of the second display unit component 216, contrast levels of the second display unit component 216, the quantity of ambient light, time of day, and/or ambient noise level, etc. The recorded data may additionally be used to, for example, evaluate refractive error testing.

In examples, the light sensor component 218 may be configured to detect the ambient light intensity around the vision screening device 200. For example, above certain brightness thresholds, the patient's pupils may constrict to the point where pupil detection is unreliable or impossible. In this instance, the server computing device(s) 202, in combination with the light sensor component 218, may determine that the ambient light is too bright and at least one of the first display unit component 214 or the second display unit component 216 may communicate to at least one of the tester or the patient use a light block, move to an environment with less ambient light, or in some way adjust the screening environment.

In examples, the computer-readable media 210 may further include a range finder component 220. The range finder component 220, in combination with the server computing device(s) 202 may be configured to determine a distance of the tester from the vision screening device 200. In some examples, the range finder component 220 may include an infrared transceiver unit, an ultrasonic transceiver unit, or another distance measuring unit known to one of skill in the art. In some examples, the patient may be positioned approximately 1 meter (m) from the vision screening device 200. However, other distances may be used to screen, such as 30 inches, 35 inches, 40 inches, or 45 inches away.

The vision screening device 200 and/or the vision screening system may be configured to provide guidance to the tester and/or the patient about how to adjust the relative positioning between the vision screening device 200 and the patient to obtain a focal distance that will yield functional images. In embodiments where the tester operates the vision screening device 200, the guidance is displayed on first display unit component 214. For example, first display unit component 214 may instruct the tester that the patient is too close, too far away, or within a proper distance. In some examples, the focal length is approximately, 0.2 m, approximately 0.3 m, approximately 0.4 m, 0.5 m, approximately 0.6 m, approximately 0.7 m, approximately 0.75 m, approximately 0.8 m, approximately 0.9 m, or approximately 1.0 m. Note that the focal length values described herein are merely examples, other focal lengths may be greater or less than those listed herein.

In further examples, the computer-readable media 210 may include a microphone component 222. The microphone component 222 may be configured to receive responses spoken by patient and generate audio data associated with the responses. For example, the patient may provide auditory responses as part of the visual acuity test and/or other vision tests described herein. For example, the patient may be asked to read an optotype, such as a letter, shown on the second display unit component 216 and the microphone component 222 may be configured to receive the patient's responses. In response, the microphone component 222 may be configured to generate audio data associated the responses and/or transmit the audio data to the vision screening system. In combination with voice recognition software, the microphone component 222 and/or the vision screening system may decode the responses to generate the audio data and may use the audio data in the various vision tests described herein.

The computer-readable media 210 may also include a wireless component 224 The wireless component 224 may be configured to connect to external databases to receive, access, and/or send screening data using wireless connections. Wireless connections can include cellular network connections and connections made using protocols such as 802.11a, b, g, and/or ac. In other examples, a wireless connection can be accomplished directly between the vision screening device 200 and an external display using one or more wired or wireless protocols, such as Bluetooth, Wi-Fi Direct, radio-frequency identification (RFID), or Zigbee. Other configurations are possible. The communication of data to an external database can enable report printing or further assessment of the patient's visual test data. For example, data collected and corresponding test results may be wirelessly transmitted and stored in a remote database accessible by authorized medical professionals.

Figure 3:
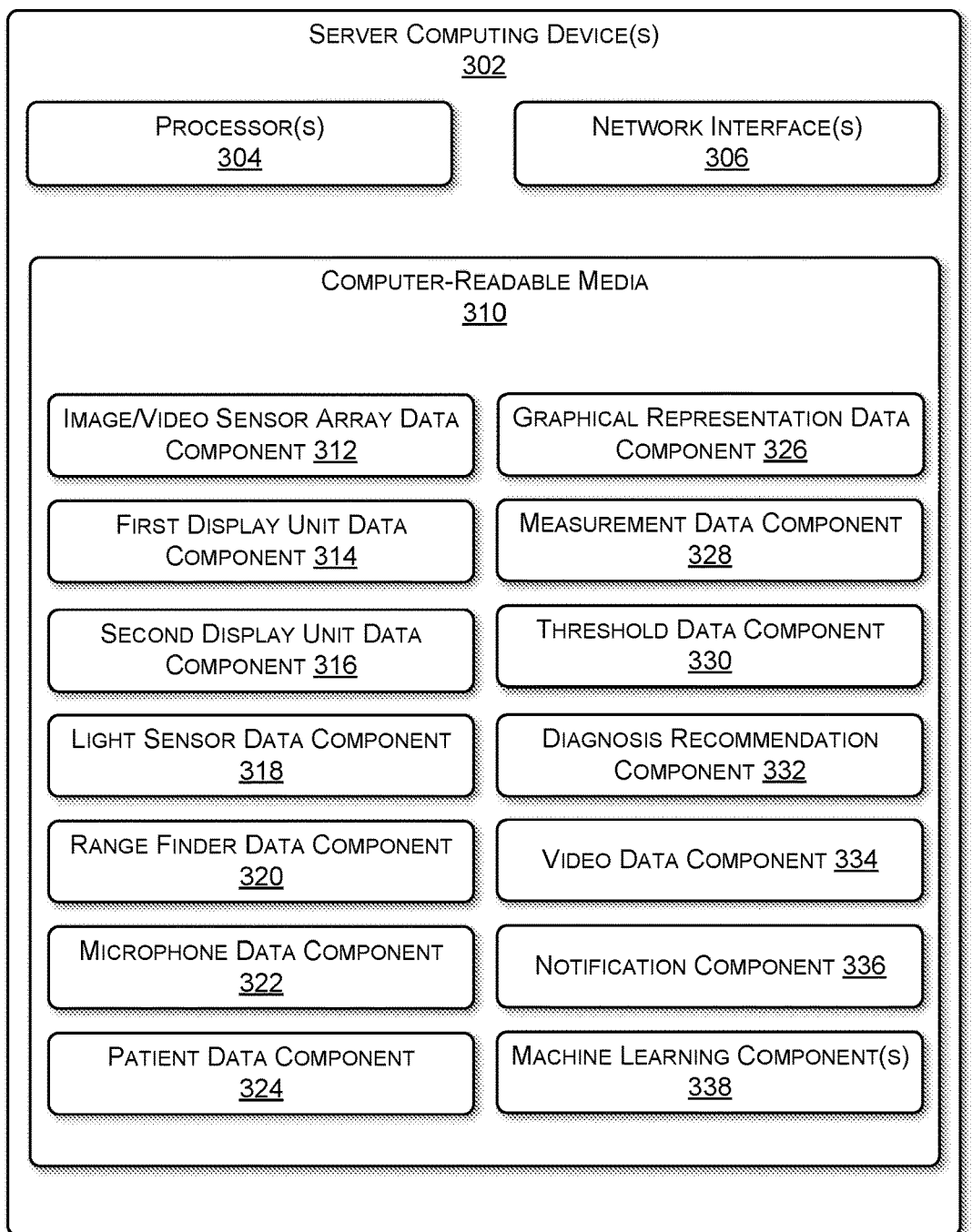
FIG. 3 illustrates an example server computing device of an example vision screening system that may be used for vision screening according to some implementations.

FIG. 3 illustrates an example server computing device 302 of a vision screening negotiation system 300 for performing techniques as described herein. As described herein, the server computing device(s) 302 ("server(s)" hereinafter) can include one or more servers or other types of computing devices that can be embodied in any number of ways. For example, in the example of a server, the modules, other functional components, and data can be implemented on a single server, a cluster of servers, a server farm or data center, a cloud-hosted computing service, a cloud-hosted storage service, and so forth, although other computer architectures can additionally or alternatively be used.

Further, while the figures illustrate the components and data of the server(s) 302 as being present in a single location, these components and data can alternatively be distributed across different computing devices and different locations in any manner. In some examples, such components and data can be distributed across user computing devices, as described herein. The functions can be implemented by one or more server computing devices, with the various functionality described above distributed in various ways across the different computing devices. Multiple server(s) 202 can be located together or separately, and organized, for example, as virtual servers, server banks and/or server farms.

In some examples, the server(s) 302 may perform the same or similar functions as the vision screening system(s) described in FIGS. 1-9. The server(s) 302 may comprise processor(s) 304 that are operatively connected to network interface(s) 306, microphone(s) 308, and a computer-readable media 310. Each processor 304 can be a single processing unit or a number of processing units and can include single or multiple computing units or multiple processing cores. The processor(s) 304 can be implemented as one or more microprocessors, microcomputers, microcontrollers, digital signal processors, central processing units, state machines, logic circuitries, and/or any devices that manipulate signals based on operational instructions. For example, the processor(s) 304 can be one or more hardware processors and/or logic circuits of any suitable type specifically programmed or configured to execute the algorithms and processes described herein. The processor(s) 304 can be configured to fetch and execute computer-readable instructions stored in the computer-readable media 310, which can program the processor(s) 304 to perform the functions described herein.

The computer-readable media 310 can include volatile and nonvolatile memory and/or removable and non-removable media implemented in any type of technology for storage of information, such as computer-readable instructions, data structures, program modules, or other data. Such computer-readable media 310 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the server(s) 302, the computer-readable media 310 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 310 can be used to store any number of functional components that are executable by the processor(s) 304. In many implementations, these functional components comprise instructions or programs that are executable by the processor(s) 304 and that, when executed, specifically configure the one or more processors 304 to perform the actions attributed above to the automated negotiation system. Functional components stored in the computer-readable media 310 can include an image/video sensor array data component 312, a first display unit data component 314, a second display unit data component 316, a light sensor data component 318, a range finder data component 320, a microphone data component 322, a patient data component 324, a graphical representation data component 326, a measurement data component 328, a threshold data component 330, a diagnosis recommendation component 332, a video data component 334, a notification component 336, and/or machine learning component(s) 338.

In examples, the computer-readable media 310 may include an image/video sensor array component 312. The image/video sensor array component 312 may be configured to receive and/or access light, image, and/or video data detected and/or generated by the vision screening device (e.g., the image/video sensor array component 212 of the vision screening device 200) associated with a patient being evaluated during the vision screening. For example, as described herein, the image/video sensor array component 212 may detect and/or generate image/video data during the vision screening used to determine initial patient data, one or more measurements associated with the body and eyes of the patient, and the like. The image/video sensor array data component 312 may be configured to receive, access, and/or store the data.

The computer-readable media 310 may further include a first display unit data component 314, a second display unit data component 316, a light sensor data component 318, a range finder data component 320, and/or a microphone data component 322. These components may be configured to receive, access, and/or store data from, for example, at least one of the image/video sensor array component 212, the first display unit component 214, the second display unit component 216, the light sensor component 218, the range finder data component 220, and/or the microphone data component 222.

In examples, the computer-readable media 310 may also include a patient data component 324. As described herein, the patient data component 324 may be configured to receive, access, store, and/or analyze various data associated with the patient in order to determine patient data for use by the vision screening system 300. For example, the patient data component 324 may be configured to receive/access patient data from the vision screening device indicating demographic information associated with the patient. For instance, the patient data component 324 may be configured to receive patient data from the vision screening device entered by the tester and indicating various characteristics of the patient (e.g., patient provided or determined otherwise), as well as a desired screening to be performed. In examples, the patient data component 324 may also be configured to receive/access patient data from a third party databased associated with the patient and/or other patients who have utilized the vision screening system 300. Still further, in examples, the patient data component 324 may be configured to receive/access image/video data from the image/video sensor array component 212 of the vision screening device and/or the image/video sensor array data component 312. The patient data component 324 may be configured to analyze the image/video data to determine certain characteristics associated with the patient, such as age, height, pupil location, and the like.

In examples, the computer-readable media 310 may also include a graphical representation data component 326. The graphical representation data component 326 may be configured to determine and/or generate one or more graphical representations for display to the patient during the vision screening test. For examples, the graphical representation data component 326 may be configured to receive and/or access patient data from the patient data component 324 to determine a characteristic and/or testing category associated with the patient (e.g., toddler, senior, near-sighted, etc.). Utilizing this information, the graphical representation data component 326 may determine a type of graphical representation to generate for display to the patient. For example, if the patient data indicates that the patient is being screened for dynamic pupil tracking, the system may generate a moving image for display to the patient in order to track how the pupil movement of the patient during the screening. The graphical representation data component 326 may further be configured to transmit information to the screening device to cause the screening device to provide an indication of the graphical representation to the patient.

In examples, the computer-readable media 310 may also include a measurement data component 328. For example, the measurement data component 328 may be configured to receive/access image/video data from the image/video sensor array component 212 of the vision screening device and/or the image/video sensor array data component 312. The measurement data component 328 may further be configured to analyze the image/video data to determine one or more measurements associated with the patient throughout the vision screening and/or in response to being displayed the graphical representation. For example, the measurement data component may be configured to analyze the image/video data to determine a location of the patient's pupils and/or lenses, a diameter of the pupils and/or lenses (e.g., indicating expansion or contraction), a motion of the pupils and/or lenses (e.g., indicating a convergence or divergence), a gaze of the patient, etc. from the data. The measurements may be determined as at points in time while the graphical representation is being displayed.

For example, the measurement data component 328 may be configured to receive/access image/video data from the image/video sensor array component 212 of the vision screening device and/or the image/video sensor array data component 312 to determine a gaze direction of the patient in response to being displayed the graphical representation. For example, the gaze of the patient may be determined by shining a light, such as an infrared light, in the direct of the patient. In response, the cornea of the patient may reflect the light and the reflection may be included, or visible, in the image or video data. The measurement data component 328 may utilize the reflection to determine a glint, or straight-line measurement, from the source of the light to the center of the eye (e.g., the origin of the reflection). As such, the measurement data component 328 may utilize this information to determine a position, location, and/or motion of the pupil at different points in time while the graphical representation is being displayed. In other examples, the measurement data component 328 may utilize the image/video data to determine the position or location of the pupil may be determined relative to the outside edges of the eye (e.g., the outline of the eye). The measurement data component 328 may utilize the measurements associated with the gaze of the patient to determine one or more locations of the patient's pupils at points in time while being displayed the graphical representation (e.g., position vs. time data points).

In examples, the computer-readable media 310 may also include a threshold data component 330. The threshold data component 330 may be configured to receive, access, and/or analyze threshold data associated with standard testing results. For example, the threshold data component 330 may be configured to access, or receive data from, a third-party database storing testing data and/or measurements, or a range of values indicating a threshold within which testing values should lie, associated with patients having normal vision health with similar testing conditions. For example, for each testing category, standard testing data may be accessed or received by the threshold data component 330 and may be utilized for comparison against the measurement data stored by the measurement data component 328. For instance, the threshold data associated with the senior testing category may include standard pupil measurements, and/or a threshold value that testing values should not exceed or fall below (e.g., a standard value range, such as the Donder's Table values described herein) for seniors when displayed each graphical representation.

Alternatively, or in addition, the threshold data component 330 may be configured to utilize one or more machine learning techniques to determine threshold data associated with each testing category and/or graphical representation. For example, the threshold data component 330 may be configured to utilize one or more trained machine learning models of the machine learning component(s) 338 to determine threshold data. For example, the machine learning component(s) 338 may be configured to access and/or receive historical vision screening data from a database, such as a screening database storing historical screening data, and may utilize this data to train one or more machine learning models to determine standard testing measurements for each testing category. For example, machine learning component(s) 338 may execute one or more algorithms (e.g., decision trees, artificial neural networks, association rule learning, or any other machine learning algorithm) to train the system to determine the one or more threshold values based on historical vision screening data. In response, the threshold data component 330 may be configured to utilize the trained models to determine one or more threshold values and/or standard values for use by the vision screening system 300.

The computer-readable media 310 may additionally store a diagnosis recommendation component 332. The diagnosis recommendation component 332 may be configured to receive, access, and/or analyze measurement data from the measurement data component 328 and/or threshold data from the threshold data component 330 for comparison. For example, the diagnosis recommendation component 332 may utilize the threshold data, learned or otherwise determined, for comparison against the measurement data to determine if the patient is exhibiting normal vision behavior (e.g., has passed or failed the vision screening), needs further screening, etc. For example, if the pupil diameter measurement(s) detected by the vision screening device, in response to the graphical representation being displayed, are within a learned or known (e.g., predetermined) threshold of the standard values (e.g., if the measurements fall within a standard range) known for patients of the same testing category, the diagnosis recommendation component 332 may generate a recommendation indicating that the patient has passed the vision screening. Alternatively, if the pupil diameter measurement(s) fall outside of the standard value range, the diagnosis recommendation component 332 may generate a recommendation indicating that the patient has failed the vision screening test and/or indicating that the patient should receive additional screening. In other examples, if the motion data (e.g., measurements indicating a location of the pupils during the screening, or gaze direction of the patient) of the patient's pupils indicate that the motion of the patient's eyes is outside of the known thresholds (e.g., the measurements associated with the gaze at the left-most, right-most, upward-most, and/or downward-most corners of the patient's gaze, the patient's gaze experiences oscillations or saccades, etc.), the diagnosis recommendation component 332 may generate a recommendation indicating that the patient receive further screening.

In examples, the computer-readable media 310 may also include a video data component 334. The video data component 334 may be configured to generate and/or store video data associated with the vision screening. For example, the video data component 334 may be configured to receive/access video data from the image/video sensor array component 212 of the vision screening device and/or the image/video sensor array data component 312 and/or measurement data of the measurement data component 328. The video data component 334 may be configured to receive and/or access the measurement data and/or analyze the video data to determine one or more data points associated with the patient, such as a direction of the patient's gaze or a location of the patient's pupils during the vision screening. The video data component 334 may be configured to utilize the data points to generate video data including the graphical representation, as well as one or more visual indicators indicating a location of the pupils throughout the vision screening. For example, the visual indicator(s) may include one or more symbols overlaying the graphical representation and indicating a location of the pupils while the graphical representation was displayed to the patient.

For example, as described herein, the measurement data component 328 may be configured to determine one or more measurements associated with the direction of the gaze of the patient during the screening. For example, the measurement data component 328 me be configured to determine the position of one or both of the patient's pupils at points in time. In some examples, the measurement data component 328 and/or the video data component 334 may be configured to analyze the image/video data component, as described herein, to determine a location or position of the patient's pupils while the graphical representation is being displayed. For example, utilizing the gaze of the patient, visible in the video/image data, the measurement data component 328 and/or the video data component 334 may determine a position or location of one or both pupils during each frame of the graphical representation that is being displayed. As such, the measurement data component 328 and/or the video data component 334 may determine position versus time data for the patient's eyes relative to the graphical representation being displayed. In addition, the video data component 334 may utilize these data points, to generate video data including the graphical representation and one or more visual indicators, overlaying the graphical representation, and indicating a location of the pupils at each frame of the graphical representation.

The video data component 334 may also be configured to provide the generated video data to the vision screening device for display to the tester. In some examples, the video data component 334 may be configured to store the video data for later access by testers, physicians, etc. In this way, the vision health of the patient may be monitored over time and more accurate and timely diagnosis recommendations may be determined.

In examples, the computer-readable media 310 may also include a notification component 336. For example, the notification component 336 may be configured to receive and/or access the diagnosis recommendation from the diagnosis recommendation component 332 and provide an indication of the diagnosis recommendation to the user conducting the vision screening, such as a tester or physician. For instance, the notification component 336 may be configured to transmit a signal to the vision screening device to cause display of a user interface, via at least one of the first display unit component 214 and/or the second display unit component 316, indicating the diagnosis recommendation, such as if the patient has passed the vision screening, failed the vision screening, and/or a recommendation for further treatment. Additionally, or alternatively, the notification component 336 may be configured to receive and/or access the measurement data from the measurement data component 328 to provide to the tester along with, or lieu of, the diagnosis recommendation. For example, the notification component 336 may be configured to transmit a signal to the vision screening device to cause display an indication of the one or more measurements via the user interface.

In examples, the computer-readable media 310 may also include one or more machine learning component(s) 338. For example, as described herein, the machine learning component(s) 338 may be configured to execute one or more algorithms (e.g., decision trees, artificial neural networks, association rule learning, or any other machine learning algorithm) to train the vision screening system 300. In examples, the machine learning component(s) 338 may execute any type of supervised learning algorithms (e.g., nearest neighbor, Naïve Bayes, Neural Networks, unsupervised learning algorithms, semi-supervised learning algorithms, reinforcement learning algorithms, and so forth). As described herein, the trained models of the machine learning component(s) 338 may be utilized by one or more components of the vision screening system 300, such as the threshold data component 330 or the diagnosis recommendation component 332, to determine various values and/or to analyze data to determine a recommendation, and the like.

Figure 4A:
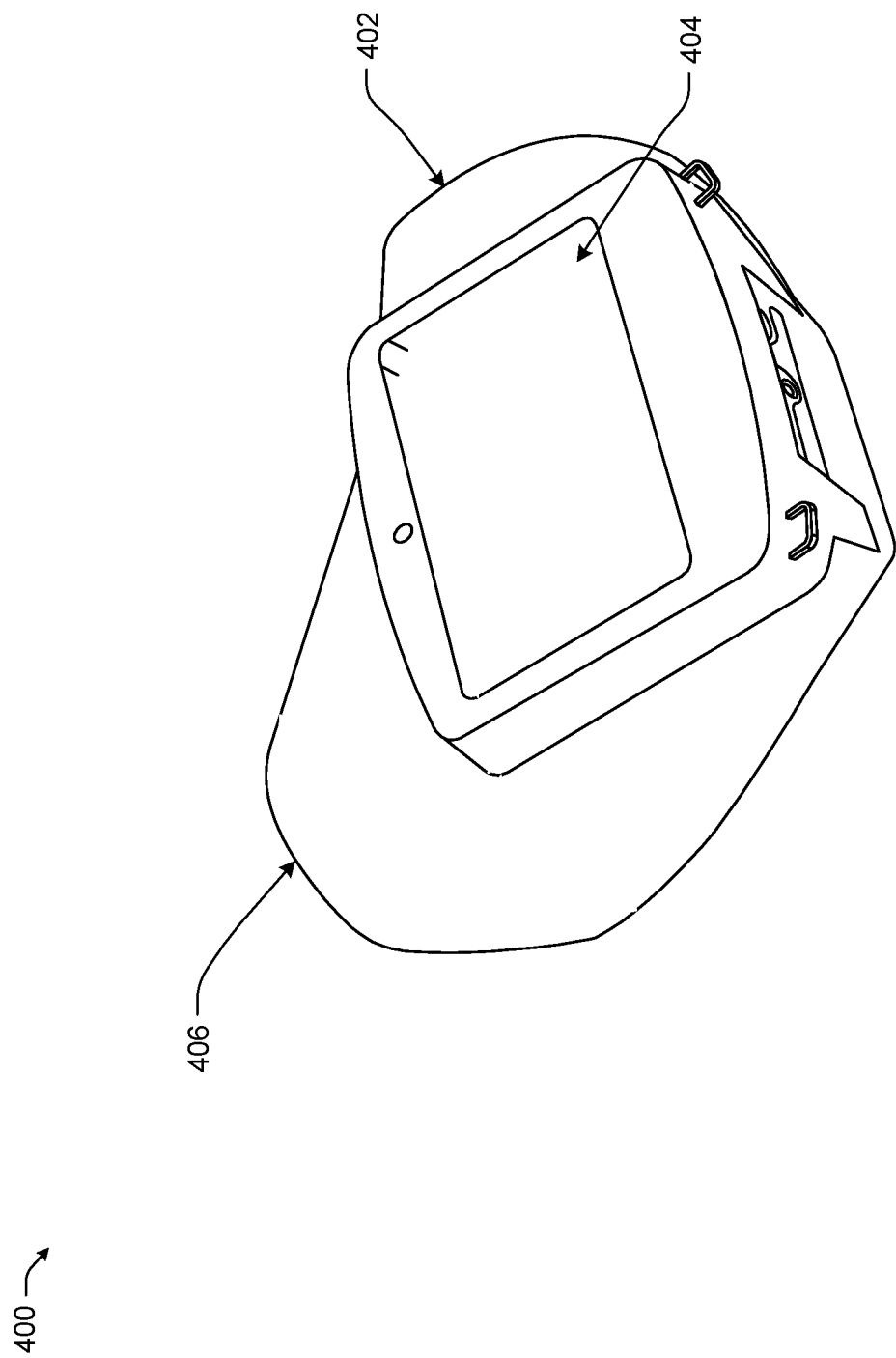
FIG. 4A illustrates a perspective view of an embodiment of a vision screening device according to some implementations.
Figure 4B:
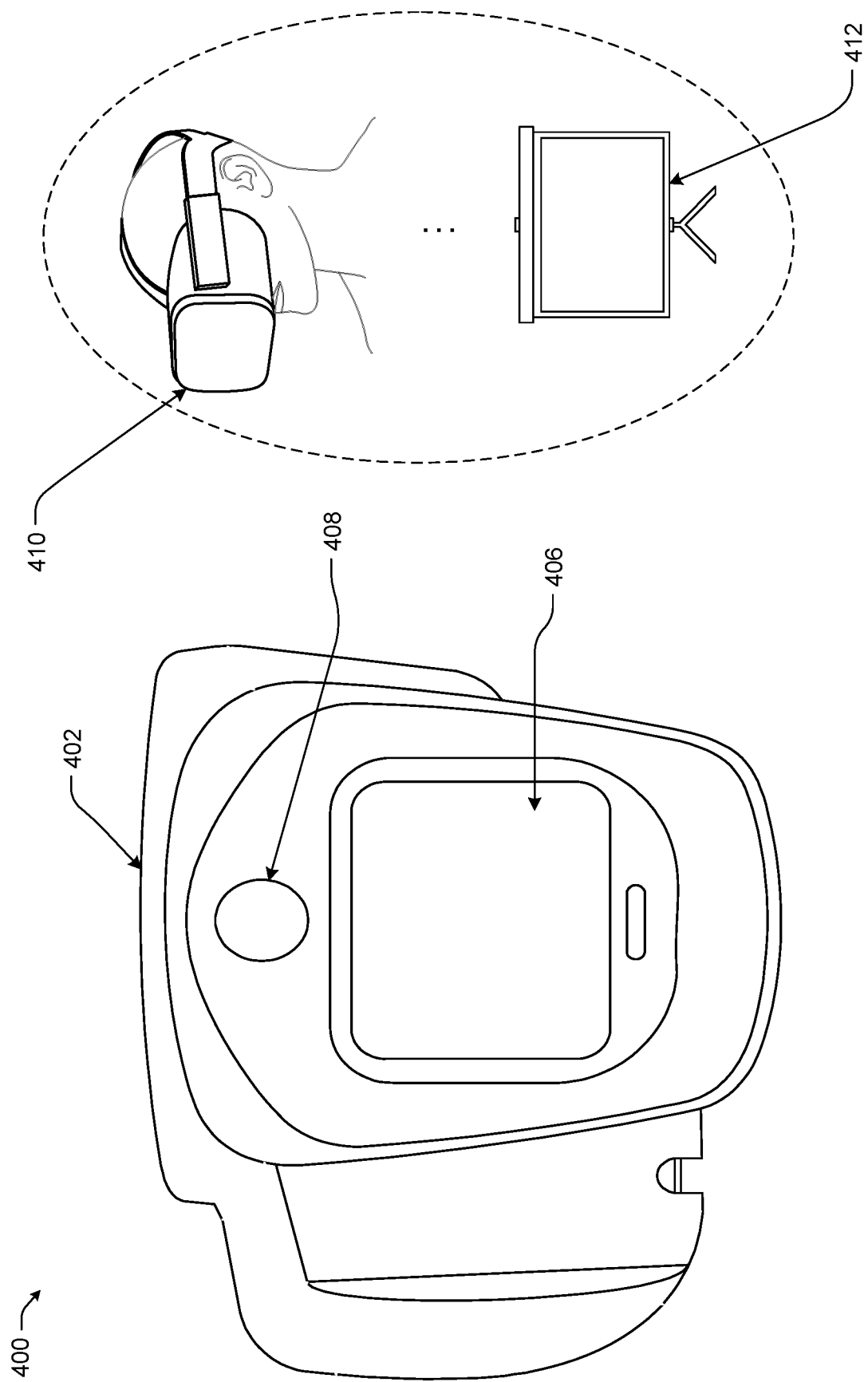
FIG. 4B illustrates another perspective view of an embodiment of the vision screening device according to some implementations.

FIGS. 4A and 4B illustrate perspective views of an embodiment of a vision screening device 400 according to some implementations. For example, the vision screening device 400 includes some or all components described above with reference to the vision screening devices of FIGS. 1-3. The vision screening device 400 may include a housing 402, a first display unit 404, a second display unit 406, and/or a range finder 408. Other embodiments can include more or fewer components.

In examples, the housing 402 may be configured to provide support for components of vision screening device 400, as well as one or more aspects configured to facilitate hand-held, or mobile, operation. In some examples, the vision screening device 400 may also be mounted on a surface, such as a tripod. In some configurations, the first display unit 404 may be configured to face a user operating the vision screening device 400, such as the tester or physician, such that the tester can navigate various control interfaces and view test results (e.g., the diagnosis recommendation). Although shown oriented at an angle relative to the tester, the first display unit 404 can have other orientations in different embodiments.

In other examples, the second display unit 406 may be positioned on an opposite end of the housing 402 such that second display unit 406 faces the patient, or person being evaluated during the vision screening, during typical operation. The second display unit 406 can include, as described herein, a display and one or more LEDs or LED arrays configured to display a graphical representation to the patient during the vision screening. An image sensor array is positioned on the interior of the housing 402 and behind the second display unit 406, or adjacent thereto. In examples, light traveling from the patient's pupils passes through the second display unit 406 where the light is received by the image sensor array. Alternatively, or in addition, the image sensor array may be positioned adjacent to second display unit 406 such that light need not pass through second display unit 406 to reach image sensor array devices.

In some examples, the housing 402 may include a third display unit (not shown). For example, the third display unit may be configured to be position near the second display unit on an opposite end of the housing and facing the patient. In this way, each of the second display unit 406 and the third display unit may be configured to display the same or different graphical representations to monitor how each eye functions together. In still other examples, the patient may be provided an augmented or virtual reality headset 410. The headset 410 may be configured to display a graphical representation to the patient without the physical limitations or display limitations of the display units. In yet other examples, a larger monitor, such as a computer monitor or projection screen 412, may be utilized for displaying graphical representations to the patient. The projection screen 412 may be located at any distance from the patient in order to induce the desired eye strain to conduct the vision screening. In these examples, the ambient light in the surrounding screening environment may be controlled to allow for the computer monitor or projection screen 412 to be utilized during the vision screening.

In examples, the range finder 408 may be configured to determine a distance from vision screening device 400 to the patient. For example, the range finder 408 may be configured to determine the distance from the patient's face to the second display unit 406. As discussed herein, the range finder 408 may be configured to determine a distance of the patient at the beginning of a test and/or to dynamically determine the patient distance throughout the various vision screenings.

Figure 5:
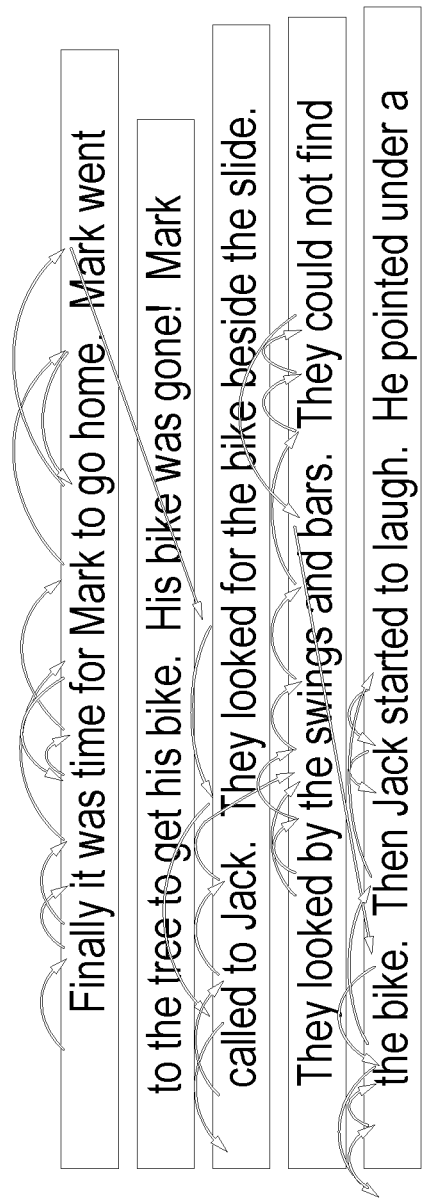
FIG. 5 illustrates an example spaghetti-type diagram according to some implementations.
Figure 6:
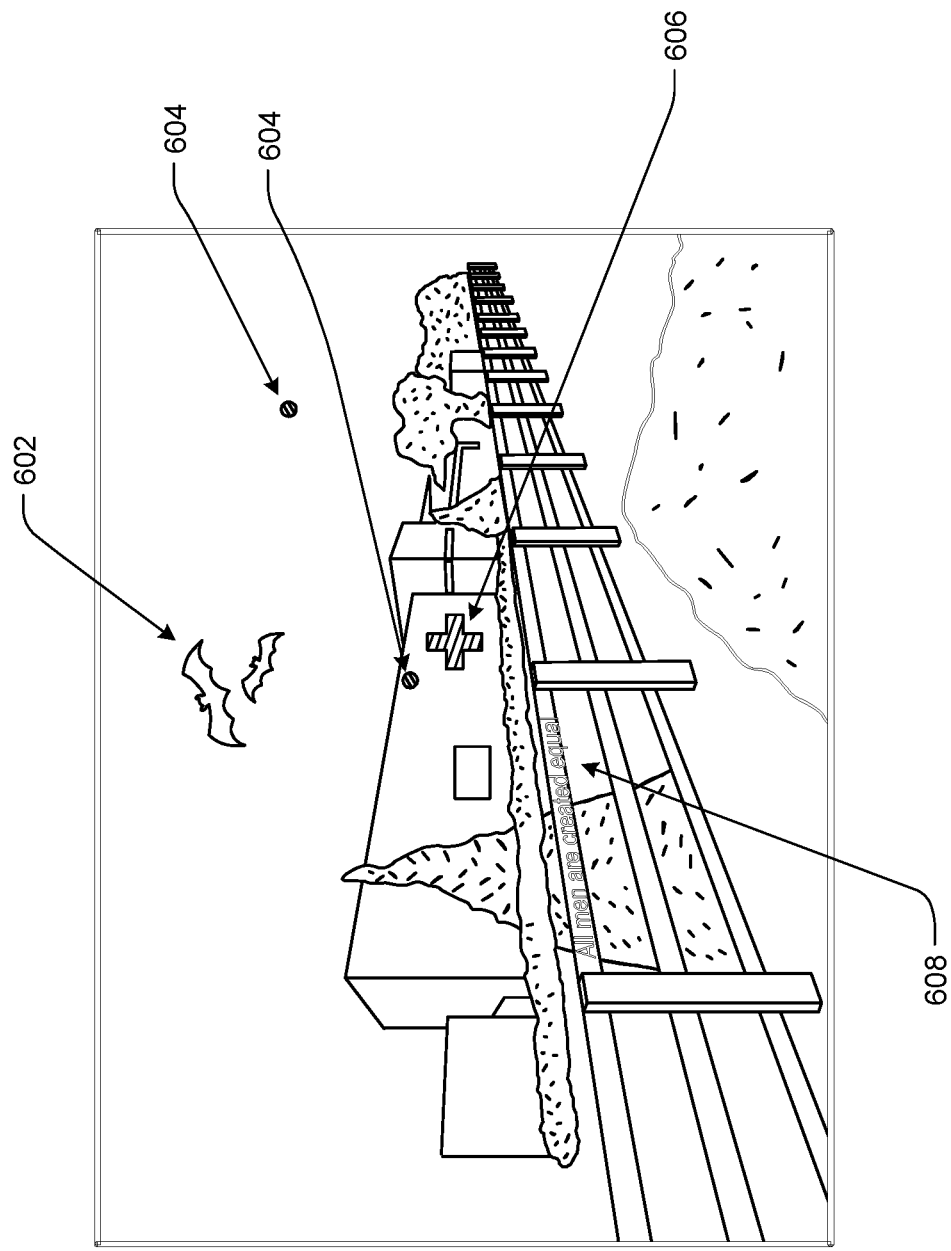
FIG. 6 illustrates an example graphical representation for display during a vision screening according to some implementations.

FIGS. 5 and 6 illustrate example graphical representations for display during a vision screening test. For example, FIG. 5 illustrates an example spaghetti-type diagram and FIG. 6 illustrates an example graphic scene, according to some implementations. As described herein, an example vision screening device (e.g., the vision screening devices described in FIGS. 4A and 4B) of a vision screening system may be configured to perform one or more vision tests on a patient and may be configured to output the results of such tests to a tester. In addition to the example vision tests described herein, the vision screening device/system may be configured to test convergence and vision efficiency during reading using binocular gaze tracking. For instance, it is understood that nearly all learning in elementary and high schools centers around a student's ability to read. Some studies have shown that 10% of children between nine and thirteen years of age suffer from moderate to marked convergence insufficiency. Unfortunately, convergence insufficiency can be difficult to evaluate, and many children are misdiagnosed with ADHD when in reality they have a convergence insufficiency or vision issue while reading. This is likely due to eyes not functioning properly when converging on a close vision activity. For example, it may be difficult for a physician or school employee administering a vision screening to accurately track the gaze of the child during a routine screening.

The vision screening system described herein may be configured to track the pupils of the patient during reading activity and to display the results on the first display 404 for a tester to review. As part of this vision test, the vision screening system may also be configured to display a spaghetti-type diagram, as illustrated in FIG. 5, along with metrics (e.g., the determine measurements, video data, and/or generated recommendation) indicating whether the patient has dyslexia, fusion, and/or convergence issues. In such examples, the vision screening device may be configured as a binocular eye tracking device (which could include virtual reality goggles 410 or other virtual reality display components) that would display a graphical representation configured to test for divergence issues for a patient of the testing category of the patient, such age appropriate text (e.g., text that the patient would be capable of reading) or displaying a target, such as via the goggles 410, and determining whether the eyes tilt inward, as normal behavior would indicate, when the target moves towards or away from the subject. In such examples, the vision screening device may be internally or externally coupled to a laptop, computer screen, or e-reader, and the vision screening device may allow for the analysis of the vision test data in real time. In particular, the vision screening device may track the patient's eyes as the patient reads the age appropriate reading material and would compare such eye movement with typical eye movement of other patients in that grade level (e.g., known values and/or threshold data).

In another example embodiment, the vision screening device may be configured to test provide a virtual reality eye exam to the patient. For instance, it is understood that most vision screening devices currently are not able to effectively screen patients having a relatively small pupil diameter, having eyes capable of a relatively high degree of accommodation (e.g., as with small children), in relatively high ambient light environments, etc. Because most known devices employ vision tests that are static (as opposed to dynamic), such devices are not configured to test for correction, reading convergence, and/or memory and cognitive decline.

The techniques described herein provide a vision screening system that may be configured to using eye tracking and algorithms and normative data for running test sequences in a virtual reality environment. This process will allow the tester to look at a spaghetti type diagram, as shown in FIG. 5, and the system may analyze the patient's eye behavior to determine the efficiency of the patient's eyes and use this information for vision therapy or corrective action. For example, the system may be configured to record the behavior and generate video data of the patient's eyes while the patient is reading the spaghetti diagram. The video data (e.g., the eye tracking data and/or other test data obtained using the vision screening device) may be analyzed to determine one or more measurements associated with the patient's eyes for comparison against known, or standard, measurements (e.g., threshold values associated with normal eye behavior) to determine if the patient's eyes are behaving in the same or similar manner as a patient having similar characteristics (e.g., a patient of the same age, height, etc.). As such, the measurements may indicate how each eye of the patient reacts to stimulus in a binocular and monocular fashion.

For example, the vision screening system may be configured to determine measurements associated with a range of motion for each eye (e.g., is the gaze of each eye able to move the full range of motion in the four cardinal directions) as the patient reads the text of the spaghetti diagram. In some examples, the system may determine measurements associated with smooth pursuit, or a determination of whether one or both eyes are able to smoothly follow a target displayed in a graphical representation (e.g., read the text of the spaghetti diagram). In this example, the system may determine measurements indicating whether the eye(s) have a stutter, or saccade (e.g., whether the eyes jump back and forth in motion). In still further examples, the system may be configured to determine measurements associated with the binocular tracking of the eye(s) indicating whether both eyes track the text of the spaghetti diagram together or whether one eye lag behind the other (e.g., does the motion of each eye indicate that the eyes are tracking in unison). As described herein, the system may be configured to determine measurements associated with one or both eyes to prevent either eye affecting the results of the other eye (e.g., one eye may help correct deficiencies of the other).

In some examples, the vision screening device may be configured to output an interactive movie script or command response application to the tester via the second display 406. Such a movie script or other video may have a length of three-minutes or less, and components from such a video as illustrated below in FIG. 6. Such an example vision test may force the patient's eye to act dynamically, and the vision screening device may generate video data of the patient's eyes during the test to determine measurements associated with the eyes while the scene is being displayed.

For example, the eye could be forced to look spatially at extremes to eliminate some of the existing accommodation limitations. As a result, the device may track the eyes with gaze tracking under dynamic conditions, so confirmation can be affirmed without a manual process. Additionally, the device may simulate potential correction so that the tester may more fully understand the characteristics of the patient's eye. With reference to the example scene illustrated in FIG. 6, as part of such a dynamic test, the vision screening device may cause the bats 602 or the dots 604 to move while tracking the patient's pupils. Such a test may evaluate the person's near and far focus. Additionally, the device may test color recognition by asking the patient to read and/or recognize the symbol 606 illustrated on the building wall. Further, the device may test for convergence and/or saccades by asking the patient to read the text 608 illustrated on the fence. Moreover, the device may test for pupil reaction by illustrating a dimly lit scene (e.g., a night scene). The device may evaluate refractive error while presenting the patient with a dynamic scene via the second display 406. In any such examples, a virtual reality vision test provided by the device evaluates not only refractive error, but also convergence insufficiency, stimulus tracking, etc. As a result of such tests, the system can track improvement or deterioration of visual or cognitive issues.

In a further example, the vision screening system may be configured to measure eccentric photo refraction with accommodation and pupil control using a tinted medium or other such medium. For instance, it is understood that when known devices are used to perform an eccentric photo refraction test on a patient, particularly on small children, the patient's eyes tend to accommodate, focusing on a near-point object. As a result, photo refraction readings using such devices tend to be inaccurate as such eye focus causes the lens in the eye to change shape. Instead, it is understood that the most accurate photo refraction readings may be obtained when the eye is in a relaxed state. Such a relaxed state may correspond to a condition in which the pupil diameter of the patient is relatively high/maximized.

As such, example vision tests described herein may include relaxing the patient's eye by presenting the patient with darkening media or glasses, e-tint (electronic tint) glasses, or a dark tinted shield which removes focus/eliminates fixation. By causing patients to wear eyeglasses made of dark but IR transparent material, experiments have shown an increase in pupil diameter over 20%. In other examples, the system described herein may be configured to monitor the pupil diameter of a patient. Once a desired (e.g., enlarged) pupil diameter is observed, the device and/or system may tag corresponding photo refraction data as being captured when the pupil diameter was above a desired diameter threshold. As such data may be more reliable/accurate, the system may use such data for generating screening results or for other purposes. In such examples, the system may be used to monitor the dynamics (e.g., the diameter) of the pupil in order to determine when to accept photo refraction data that is being captured on a substantially continuous basis.

In still further examples, the system described herein may be configured to output a relaxing stimulus (e.g., a graphical representation including calm beach/ocean view, an illustration of a bunny, etc.) via the second display 406, the headset 410, and the like. As the patient views the stimulus, his/her pupils will dilate as a natural response to the patient feeling happy and/or relaxed. Such dilation will eliminate at least some of the accommodation such that more reliable accurate photo refraction data may be obtained. Yet another alternative example includes placing a substantially opaque hood around the face of the evaluated person beyond the range of one or more sensors of the device in order to eliminate the effect of ambient light while capturing photo refraction data.

In an additional example, the vision screening system may be configured to accurately measure eccentric photo refraction even while the patient accommodates during the vision test. For instance, it is understood that the lens of a small child's eye is typically very pliable, often providing children with more than 10 diopters of accommodation. Thus, when a small child is being tested for refractive error, the shape of the child's eye lens may change dramatically when the child focusses on a target of visual stimulus. As a result, most known devices may not be configured to accurately determine whether, for example, the child has normal vision, or if the child is farsighted and is accommodating.

As such, the techniques described herein may be configured to provide different focused and blurred (e.g., fogged) images to the patient via the second display 406. Such blurred images or other such fogged stimuli may cause the patient's eye to relax. The device and/or system may also capture a series of refractive error measurements during this process. In particular, the device may capture refractive error measurements while the various focused and blurred images are presented to the patient. As a result, the measurements will have large variations in values due to some measurements corresponding to a pre-accommodation condition of the patient's eye lens, and other measurements corresponding to a post accommodation condition of the patient's eye lens. The system may use one or more algorithms, machine learning techniques, neural networks, look-up tables and/or other components to analyze the refractive error measurement data to more accurately determine, for example, the patient's proper eyewear prescription.

In some such examples, the device may output a stimulus via the second display 406 that may cause the patient to gaze near and far to send the eye into two states. The device may also capture a series of refractive error measurements during this process. In particular, the device may capture refractive error measurements while the eye of the patient is in each of the respective states, and while the eye transitions between the two states. The device may use one or more algorithms, machine learning techniques, neural networks, look-up tables and/or other components to analyze such refractive error measurement data to more accurately determine, for example, the patient's proper eyewear prescription. In any such examples, the device may comprise an eccentric photo refractor configured to present a video or other such stimulus to initiate relaxation of each eye of the patient so that corresponding photo refraction readings can be obtained in both relaxed and accommodated states of the eye.

In yet another example, the vision screening device may comprise a visual acuity system that is configured to use eye tracking and DLP projection in order to determine a patient's ability to identify characters at a particular distance. For instance, it is understood that visual acuity screening can be time consuming and inaccurate in certain environments. Additionally, known vision screening devices are often not well suited for accurately testing visual acuity. As such, the system described herein may be configured to project a graphical representation including a visual acuity motion stimulus test on a projected surface and/or onto a stationary surface such as a building wall or a screen, such as projector screen 412. The projected images may provide a dynamic (e.g., lateral) stimulus, and the velocity, direction, lateral movement, and other performance metrics of the eye can be tracked and/or otherwise determined by the device/system as such stimuli are observed by the patient. The device may be configured to record these parameters and/or to compare the rate of change of these parameters to empirical data or known standards, as described herein. In some examples, such dynamic stimulus tests facilitated by the system replace the classic Snellen chart, as such Snellen-based evaluations of visual acuity are relatively subjective. Additionally, as part of such a dynamic stimulus test, the device may be configured to flash an optotype to the patient so that the patient can confirm a target Snellen equivalent.

In examples, the aspect and/or other characteristics of the stimulus can be scalable through distance projection on a surface, such as projection screen 412. For example, visual acuity tests may be performed at 4 feet, or a more arduous field of view test at 8 feet. The wider projection could tax the eye more in its field of view when the device projects a lateral stimulus at such ranges. In such tests, the device may track the eye metrics of speed, direction, velocity, saccades, etc. The device may also be operable to perform such visual acuity tests in different dedicated operating modes that are tuned based on the age of the patient (e.g., a "child" mode, an "adult" mode, a "geriatric" mode, or other testing category) and/or based on the skill of the tester (e.g., an "optometrist" mode, a "streamlined" mode, etc.). In addition, the vision screening device could automatically scale the test with a measurement of wall or surface distance.

In any of the examples described herein, the vision screening device may include a DLP projection unit on one side and an eye tracker for each eye on the other side. Additionally, in some examples, an additional computational device such as an iPad, a mobile phone, a tablet computer, a laptop computer, or other such processor or device may be used in combination with and/or in place of the vision screening device. Such an additional device be configured to track the eyes with software and/or with the use of an associated image capture device (e.g., a camera). Accordingly, the various systems described herein may be embodied in a single unit or in separate devices or components.

Figure 7:
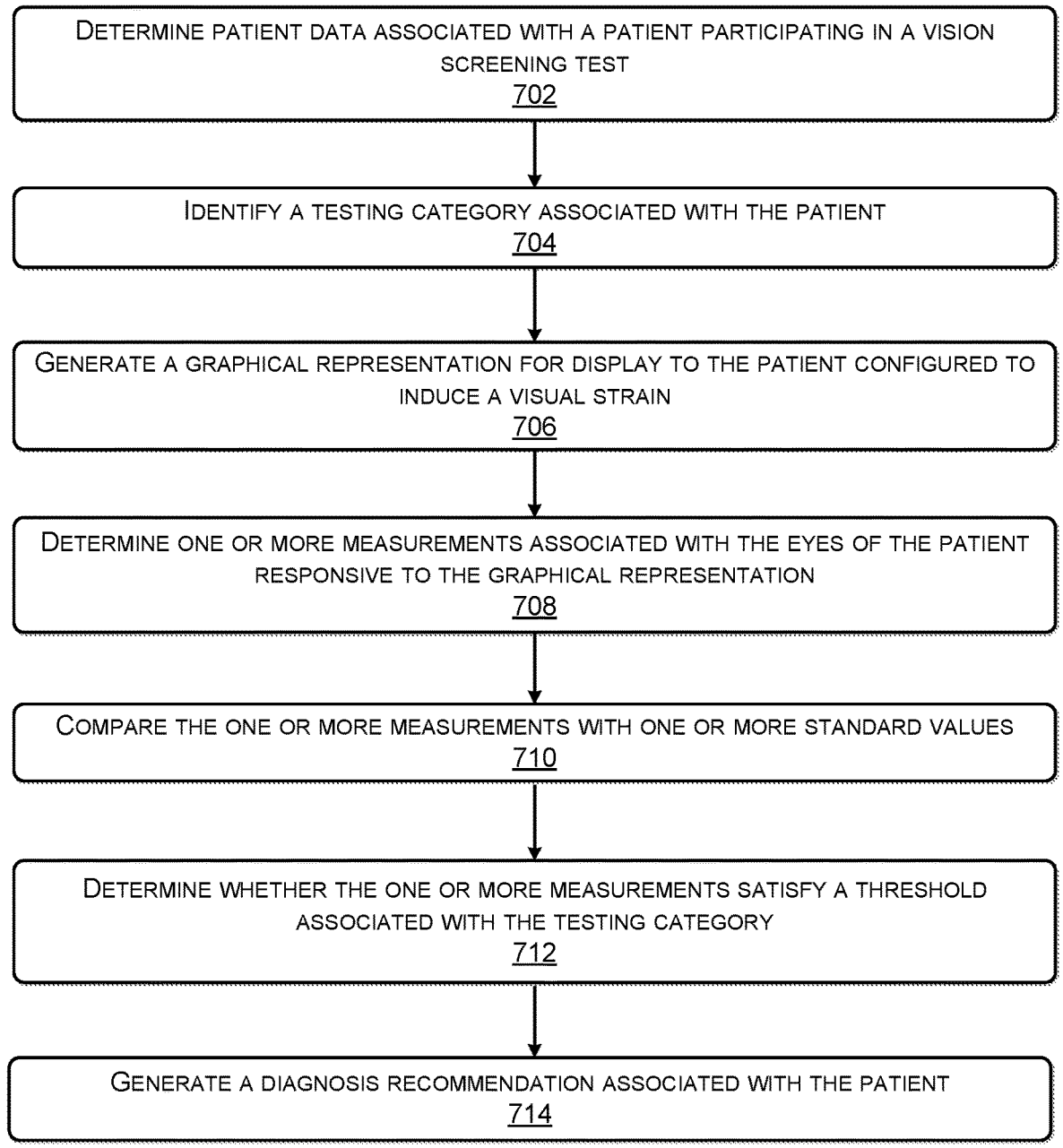
FIGS. 7 and 8 illustrate example flow diagrams for vision screening according to some implementations.
Figure 8:
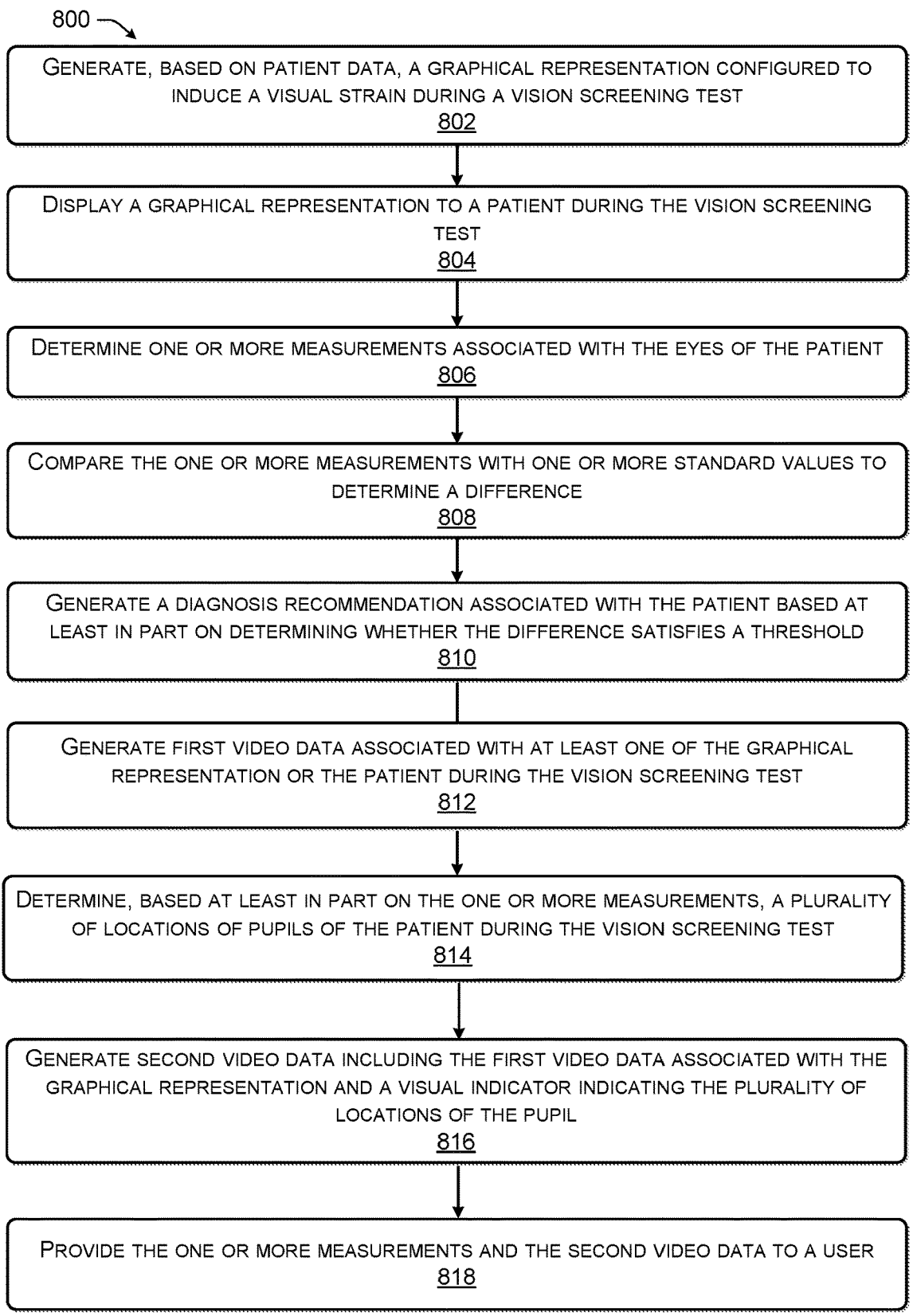

Further, it is understood that in examples, the vision screening device and/or vision screening system may be configured to perform multiple vision screening tests on the patient. Such tests may include, for example, but not be limited to:
  Accommodation Test—have the patient look near and far to measure accommodative facility of each eye
  Color Test-standard enchroma test
  Target tracking Efficiency Test—tracks eye binocularly dynamically to target
  Reading with Eye Tracking Test-spaghetti diagram visual Reading vs Metrics
  Fixations/100 words: this is a measure of how often the eye stops per every 100 words.
  Regressions/100 words: this is a measure of how often the eye moves backwards without re-reading. (e.g., unconscious backward movement)
  Directional attack percentage: this is a measure of the tendency to perceive content in a left to right manner. This metric measures the ratio between forward to backward saccades (ratio of fixations to regressions %)
  Average Span of Recognition: this measures the amount of words comprehended in a single fixation (fixations/total words)
  Average duration of the fixations: measuring mean fixation time
  Words/minute rate w comprehension-right now words/minute.
  Vergence Facility—ability to fuse at close/reading range with optical power
  Convergence Insufficiency Test—test of close range binocular fusion
  Dynamic Cover Test—refract then cover weaker eye to determine phoria or tropia
  Depth perception Test—can disseminate near far objects
  Visual Acuity—Snellen or Lea symbols FIGS. 7 and 8 illustrate various flow diagrams of example processes for vision screening, as described herein. The processes 700 and 800 are illustrated as collections of blocks in logical flow graphs, which represent sequences of operations that can be implemented in hardware, software, or a combination thereof. In the context of software, the blocks represent computer-executable instructions stored on one or more computer-readable storage media that, when executed by processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes. In some embodiments, one or more blocks of the process can be omitted entirely. Moreover, the processes 700 and 800 can be combined in whole or in part with each other or with other processes.

FIG. 7 illustrates an example process 700 for vision screening according to some implementations. In some examples, operations described below can be performed by a system including local computing device(s) and/or remote computing device(s) that are in communication with the local computing device(s) (e.g., in a distributed configuration).

At operation 702, the system may determine patient data associated with a patient participating in a vision screening test. As described herein, a patient being evaluated by the vision screening system may provide information to the system. In some examples, the patient may manually enter such information via one or more touchscreens or other input devices of the vision screening device. In additional examples, a physician or other user of the device may manually enter such information via such input devices. Additionally, or alternatively, the system may receive and/or access data associated with the patient from a database of the system storing information associated with patients. The received and/or accessed data may be analyzed by the system to determine one or more characteristics associated with the patient, such as demographic information, physical characteristics of the patient, etc. Still further, in some examples, the system may generate image or video data associated with the patient and may analyze the image/video data to determine the characteristics associated with the patient.

At operation 704, the system may identify a testing category associated with the patient. For example, the system may determine, based at least in part on the patient data, a category which the patient belongs to. The testing categories may include, but not be limited to, age categories, gender categories, physical characteristic categories (e.g., height, pupil distance, etc.).

At operation 706, the system may generate a graphical representation for display to the patient configured to induce a visual strain. For example, as described herein, based at least in part on the patient data and/or the testing category, the system may determine and/or generate a graphical representation configured to induce a strain on the vision or eyes of the patient. For example, if the system determines that the patient is a teenager, the system may determine a graphical representation, from among pre-generated graphical representations, or generate a graphical representation that will strain the vision of the patient in order to perform the desired vision screening. As an example, if the system wants to test how the patient's eyes behave while reading, the graphical representation may include a paragraph of text. As another example, if the system wants to test the limits of motion of the patient's eyes, the graphical representation may include a dynamic video.

At operation 708, the system may determine one or more measurements associated with the eyes of the patient responsive to the graphical representation. For example, as described herein, the system may be configured to record image/video data of the patient during the vision screening. The system may then analyze the image/video data to determine one or more measurements associated with the eyes of the patient. The measurements may include, but not be limited to measurements associated with a gaze of the patient, a location of the pupils, a diameter of the pupils, a diameter of the lens, motion data, etc.

At operation 710, the system may compare the one or more measurements with one or more standard values. For example, the system may be configured to receive, access, and/or determine known standard values, indicating values of known standard behavior for patients being screened. The system may then compare the one or more determined measurements with the standard values to determine if the patient is exhibiting normal vision behavior. As described herein, the standard values may be received and/or accessed from a data based and/or may be determined utilizing historical screening data and/or one or more machine learning techniques.

At operation 712, the system may determine whether the one or more values satisfy a threshold associated with the testing category. As described in operation 710, the system may be configured to compare the one or more measurements associated with the patient with one or more standard values. The system may also be configured to receive, access, or determine a threshold range within which the one or more measurements should lie. Based on the comparison, the system may determine whether the one or more measurements lie within the threshold range of normal behavior. In some examples, the known values and/or thresholds may be associated with a testing category. For example, standard values may be associated with each testing category associated with each age range (e.g., the standard values of a toddler may differ from the standard values of an adult).

At operation 714, the system may generate a diagnosis recommendation associated with the patient. For example, as described at operation 712, the system may determine whether the one or more measurements satisfy the threshold of standard behavior. Based on this determination, the system may generate a recommendation indicating whether the patient has passed or failed the vision screening, and/or whether the patient requires additional screening. As described herein, the system may also utilize historical screening data and/or one or more machine learning techniques to generate the recommendation. For example, based on historical patient data, the system may train one or more machine learning models. The system may then utilize the trained models to determine if the patient's measurements exceed learned thresholds determined to be associated with normal vision behavior. Alternatively, or in addition, the system may compare the patient's measurements with previous screening behavior and generate a recommendation based on a similarity of the measurements to those of similar previous screenings (e.g., the system may generate a substantially similar recommendation if the patient's measurements are similar to those of previous screenings). The system may provide the recommendation, along with the one or more measurements, video data, and the like, to a user, such as a tester or physician conducting the screening and/or operating the screening device, for review.

FIG. 8 illustrates an example process 800 for vision screening according to some implementations. In some examples, operations described below can be performed by a system including local computing device(s) and/or remote computing device(s) that are in communication with the local computing device(s) (e.g., in a distributed configuration).

At operation 802, the system may generate, based on patient data, a graphical representation configured to induce a visual strain during a vision screening test. As described herein, the system may be configured to receive patient data from a patient, such as a patient being evaluated by the vision screening system. In some examples, the system may also receive and/or access data associated with the patient from a database of the system storing information associated with patients. The received and/or accessed data may be analyzed by the system to determine one or more characteristics associated with the patient, such as demographic information, physical characteristics of the patient, etc. Still further, in some examples, the system may generate image or video data associated with the patient and may analyze the image/video data to determine the characteristics associated with the patient. Based at least in part on the patient data, the system may then determine and/or generate a graphical representation configured to induce a strain on the vision or eyes of the patient during the vision screening test.

At operation 804, the system may display the graphical representation to a patient during the vision screening test. As described herein, the system may be configured to display the graphical representation to the patient in a number of ways. For example, the system may be configured to cause the graphical representation to be displayed to the patient via a display unit of a vision screening device in communication with the system. The system may also be configured to cause the graphical representation to be displayed to the patient via a virtual reality or augmented reality headset or via projection onto an external surface, such as a projector screen or wall.

At operation 806, the system may determine one or more measurements associated with the eyes of the patient. For example, as described herein, the system may be configured to record image/video data of the patient during the vision screening. The system may then analyze the image/video data to determine one or more measurements associated with the eyes of the patient responsive to the graphical representation. The measurements may include, but not be limited to measurements associated with a gaze of the patient, a location of the pupils, a diameter of the pupils, a diameter of the lens, motion data, etc.

At operation 808, the system may compare the one or more measurements with one or more standard values to determine a difference. For example, the system may be configured to receive, access, and/or determine known standard values, indicating values of known standard behavior for patients being screened. The system may then compare the one or more determined measurements with the standard values, or a threshold range of values, to determine if the patient is exhibiting normal vision behavior. As described herein, the standard values and threshold ranges may be received and/or accessed from a database and/or may be determined utilizing historical screening data and/or one or more machine learning techniques. For example, the system may be configured to compare the one or more measurements associated with the patient with one or more standard values to determine a difference (e.g., to determine whether the one or more measurements lie within the threshold range of normal behavior).

At operation 810, the system may generate a diagnosis recommendation associated with the patient based at least in part on determining whether the difference satisfies a threshold. For example, as described at operation 808, the system may determine whether the one or more measurements satisfy the threshold of standard behavior (e.g., whether the difference between the measurements and the standard values lies within the threshold range). Based on this determination, the system may generate a recommendation indicating whether the patient has passed or failed the vision screening and/or whether the patient requires additional screening. As described herein, the system may also utilize historical screening data and/or one or more machine learning techniques to generate the recommendation. The system may provide the recommendation, along with the one or more measurements, video data, and the like, to a user, such as a tester or physician conducting the screening and/or operating the screening device, for review.

At operation 812, the system may generate first video data associated with at least one of the graphical representation or the patient during the vision screening test. For example, the vision screening device may be configured to record (e.g., generate video data) the graphical representation being displayed and/or the patient during the vision screening test. Based on the video data, the system may determine measurements associated with the eyes of the patient, such as measurements associated with the pupils, lenses, and the like, at points in time during the screening and responsive to being displayed the graphical representation.

At operation 814, the system may determine, based at least in part on the one or more measurements, a plurality of location of pupils of the patient during the vision screening test. For example, as described at operation 812, the system may generate video data associated with the patient and/or the graphical representation during the vision test. The system may utilize the video data to determine a location of the patient's pupils throughout the vision screening and at points in time of being displayed the graphical representation. For example, the location of the pupils may indicate the motion of the patient's eyes during the vision screening test, such as when the patient is being displayed a video clip.

At operation 816, the system may generate second video data including the first video data associated with the graphical representation and a visual indicator indicating the plurality of locations of the pupil. For example, the system may be configured to generate a second video including the graphical representation and one or more indicators of the location of the patient's pupils during the vision screening test and/or responsive to being displayed the graphical representation. For example, the video may include the graphical representation, such as a video clip displayed to the patient, and one or more dots indicating the location of the patient's pupils as the video played. The video may be used to determine whether the patient's eyes are exhibiting normal behavior responsive to the video clip (e.g., are the eyes tracking the objects being displayed properly, is the motion normal, etc.).

At operation 818, the system may provide the one or more measurements and the second video data to a user. For example, as described herein, the system may be configured to provide the one or more measurements and/or the second video data to the user, such as the tester or physician conducting the screening and/or operating the screening device. For example, the system may be configured to cause the one or more measurements and/or the second video data to be displayed to the user via a display unit of the screening device.

It should be noted that reference to an "embodiment" in this document does not limit the described elements to a single embodiment; all described elements may be combined in any embodiment in any number of ways. Furthermore, for the purposes of interpreting this specification, the use of "or" herein means "and/or" unless stated otherwise. The use of "a" or "an" herein means "one or more" unless stated otherwise. The use of "comprise," "comprises," "comprising," "include," "includes," and "including" are interchangeable and not intended to be limiting. Also, unless otherwise stated, the use of the terms such as "first," "second," "third," "upper," "lower," and the like do not denote any spatial, sequential, or hierarchical order or importance, but are used to distinguish one element from another. It is to be appreciated that the use of the terms "and/or" and "at least one of", for example, in the cases of "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It should also be appreciated by those skilled in the art that any block diagrams, steps, or sub-processes herein represent conceptual views of illustrative systems embodying the principles of the present subject matter. Similarly, it may be appreciated that any flow charts, flow diagrams, state transition diagrams, pseudo code, and the like represent various processes which may be substantially represented in computer readable medium and so executed by a computer or processor, whether or not such computer or processor is explicitly shown. The order in which the methods are described are not intended to be construed as a limitation, and any number of the described method blocks can be deleted, moved, added, subdivided, combined, and/or modified in any order to implement the methods, or an alternative combination or sub-combinations. Also, while steps, sub-processes or blocks are at times shown as being performed in series, some steps, sub-processes or blocks can instead be performed in parallel, or can be performed at different times as may be recognized by a person of ordinary skill in the art. Further any specific numbers noted herein are only examples; alternative implementations can employ differing values or ranges. Furthermore, the methods and implementations described herein can be implemented in any suitable hardware, software, firmware, or combination thereof. For example, the methods and implementations described herein can utilize a number of user interfaces, including but not limited to any or all of user interfaces rendered via a device terminal (e.g., a keypad, a touchscreen, etc.), software installed on user devices (e.g., a mobile application, messaging services, etc.), a tablet computer, or a web interface. Furthermore, these user interfaces are often but not always supported by Internet cloud services.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A system comprising:
   memory;
   one or more processors; and
   one or more computer-executable instructions stored in the memory and executable by the one or more processors to perform operations comprising:
      determining patient data associated with a patient participating in a vision screening test;
      identifying, based at least in part on the patient data, a testing category associated with the patient;
      generating, based at least in part on at least one of the patient data or the testing category, a graphical representation for display to the patient, the graphical representation including at least one object configured to cause a change in an eye of the patient;
      generating video data associated with at least one of the graphical representation or the patient during the vision screening test;
      determining one or more measurements associated with the eye of the patient responsive to the graphical representation, wherein:
         the one or more measurements include at least one of a shape of a lens of the eye, a diameter of a pupil of the eye, or a convergence of the pupil, and
         the one or more measurements are determined based at least in part on the video data;
      determining whether the one or more measurements satisfy a threshold; and
      based at least in part on determining whether the one or more measurements satisfy the threshold, generating a diagnosis recommendation associated with the patient.

2. The system of claim 1, wherein the one or more measurements include at least one of a speed or a position of a pupil of the eye and wherein one or more measurements are determined based at least in part on the video data.

3. The system of claim 2, wherein the video data is first video data, and the operations further comprising:
   determining, based at least in part on the one or more measurements, a plurality of locations of the pupil of the patient during the vision screening test; and
   generating, second video data including the first video data associated with the graphical representation and a visual indicator indicating the plurality of locations of the pupil.

4. The system of claim 2, wherein the change in the eye of the patient includes at least one of a first movement of the pupil from proximate a left-most position of the pupil to proximate a right-most position of the pupil or a second movement of the pupil from proximate a top-most position of the pupil to proximate a bottom-most position of the pupil.

5. The system of claim 1, the operations further comprising displaying the one or more measurements to a user in conjunction with the diagnosis recommendation.

6. A system comprising:
   memory;
   one or more processors; and
   one or more computer-executable instructions stored in the memory and executable by the one or more processors to perform operations comprising:
      generating a graphical representation including at least one object configured to cause a change in an eye of the patient;
      displaying the graphical representation to a patient during a vision screening test;
      determining one or more measurements associated with the eye of the patient during the vision screening test;
      determining whether the one or more measurements satisfy a threshold; and
      based at least in part on determining whether the one or more measurements satisfy the threshold, generating a diagnosis recommendation associated with the patient.

7. The system of claim 6, the operations further comprising:
   receiving patient data associated with the patient; and
   determining, based at least in part on the patient data, the graphical representation.

8. The system of claim 6, wherein the change in the eye of the patient includes at least one of a first movement of a pupil of the eye from proximate a left-most position of the pupil to proximate a right-most position of the pupil or a second movement of the pupil from proximate a top-most position of the pupil to proximate a bottom-most position of the pupil.

9. The system of claim 6, the operations further comprising generating video data associated with at least one of the graphical representation or the patient during the vision screening test.

10. The system of claim 9, wherein the video data is first video data, and the operations further comprising:
    determining, based at least in part on the one or more measurements, a plurality of locations of a pupil of the eye of the patient during the vision screening test; and
    generating, second video data including the first video data associated with the graphical representation and a visual indicator indicating the plurality of locations of the pupil.

11. The system of claim 6, wherein the one or more measurements include at least one of a speed of a pupil of the eye, a position of the pupil, a shape of a lens of the eye, a diameter of the pupil, or a convergence of the pupil, and
    wherein the one or more measurements are determined based at least in part on video data, associated with the eye of the patient, captured as the patient views the graphical representation.

12. A method, comprising:
    generating, based at least in part on patient data, a graphical representation including at least one object configured to cause a change in an eye of the patient during a vision screening test, wherein the change in the eye of the patient includes at least one of a first movement of a pupil of the eye from proximate a left-most position of the pupil to proximate a right-most position of the pupil or a second movement of the pupil from proximate a top-most position of the pupil to proximate a bottom-most position of the pupil;

displaying the graphical representation to a patient during the vision screening test;

determining one or more eye measurements, wherein the one or more eye measurements are associated with the eye of the patient as the patient views the graphical representation;

comparing the one or more measurements with one or more predetermined values to determine a difference; and determining whether the difference satisfies a threshold.

13. The method of claim 12, further comprising generating a diagnosis recommendation associated with the patient based at least in part on the determining whether the difference satisfies the threshold.

14. The method of claim 12, further comprising:

generating video data associated with at least one of the graphical representation or the patient during the vision screening test, and determining the one or more measurements based at least in part on the video data.

15. The method of claim 14, wherein the video data is first video data, and further comprising:

determining, based at least in part on the one or more measurements, a plurality of locations of a pupil of the patient during the vision screening test; and generating, second video data including the video data associated with the graphical representation and a visual indicator indicating the plurality of locations of the pupil.

16. The method of claim 12, wherein the one or more measurements further include at least one of a speed of the pupil, a velocity of the pupil, motion of the pupil, a shape of a lens of the patient, a diameter of the pupil, or a convergence of the pupil, and wherein the one or more measurements are determined based at least in part on video data, associated with the eye of the patient, captured as the patient views the graphical representation.

* * * * *